US011622990B2

(12) United States Patent
Lu et al.

(10) Patent No.: US 11,622,990 B2
(45) Date of Patent: Apr. 11, 2023

(54) VAP POLYPEPTIDE AND USE THEREOF IN PREPARATION OF DRUG FOR TARGETED DIAGNOSIS AND TREATMENT OF TUMOR

(71) Applicant: FUDAN UNIVERSITY, Shanghai (CN)

(72) Inventors: Weiyue Lu, Shanghai (CN); Danni Ran, Shanghai (CN); Jiani Mao, Shanghai (CN); Cao Xie, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 166 days.

(21) Appl. No.: 16/467,149

(22) PCT Filed: Dec. 6, 2017

(86) PCT No.: PCT/CN2017/114796

§ 371 (c)(1),
(2) Date: Jun. 6, 2019

(87) PCT Pub. No.: WO2018/103660

PCT Pub. Date: Jun. 14, 2018

(65) Prior Publication Data

US 2019/0314446 A1 Oct. 17, 2019

(30) Foreign Application Priority Data

Dec. 7, 2016 (CN) .......................... 201611115191.1

(51) Int. Cl.

| | |
|---|---|
| ***A61K 38/08*** | (2019.01) |
| ***A61K 47/64*** | (2017.01) |
| ***C07K 7/06*** | (2006.01) |
| ***A61K 9/127*** | (2006.01) |
| ***A61K 31/337*** | (2006.01) |
| ***A61K 31/42*** | (2006.01) |
| ***A61K 31/64*** | (2006.01) |
| ***A61K 31/704*** | (2006.01) |
| ***A61K 47/34*** | (2017.01) |
| ***A61K 49/14*** | (2006.01) |
| ***A61K 39/00*** | (2006.01) |
| *A61K 9/107* | (2006.01) |

(52) U.S. Cl.

CPC .............. *A61K 38/08* (2013.01); *A61K 9/127* (2013.01); *A61K 31/337* (2013.01); *A61K 31/42* (2013.01); *A61K 31/64* (2013.01); *A61K 31/704* (2013.01); *A61K 39/0011* (2013.01); *A61K 47/34* (2013.01); *A61K 47/64* (2017.08); *A61K 49/14* (2013.01); *C07K 7/06* (2013.01); *A61K 9/107* (2013.01)

(58) Field of Classification Search

CPC ........ A61K 38/08; A61K 47/64; A61K 49/14; A61K 47/34; C07K 7/06; A16K 51/088
See application file for complete search history.

(56) References Cited

U.S. PATENT DOCUMENTS

2008/0003200 A1* 1/2008 Arap ...................... A61K 47/64 514/1.2

OTHER PUBLICATIONS

Ran et al., "GRP78 enabled micelle-based glioma targeted drug delivery", Journal of Controlled Release, Available online Mar. 23, 2017, pp. 120-131 (Year: 2017).*
Jia et al., "Site-specific Characterization of D-Amino Acid Containing Peptide Epimers by Ion Mobility Spectrometry", Anal. Chem., 2014, 2972-2981 (Year: 2014).*
Chen et al., "Improving Binding Affinity and Stability of Peptide Ligands by Substituting Glycines with D-Amino Acids", ChemBioChem, 2013, 1316-1322 (Year: 2013).*
Mandelin et al. "Selection and identification of ligand peptides targeting a model of castrate-resistant osteogenic prostate cancer and their receptors", PNAS, Mar. 24, 2015, pp. 3776-3781 (Year: 2015).*
Biosyn "Retro Inverso Peptides", https://www.biosyn.com/tew/retro-inverso-peptides.aspx, Apr. 6, 2014, 1 page (Year: 2014).*
Toseland ("Fluorescent labeling and modification of proteins", J. Chem. Biol., 2013, 85-95) (Year: 2013).*
Baya ("New Polyethylene Glycols (PEG) as versatile biochemical linkers", tebu-bio, 2016, pp. 1-4). (Year: 2016).*
Feng et al. "Inspiration from the mirror: D-amino acid containing peptides in biomedical approaches", BioMol Concepts, 2016, 179-187 (Year: 2016).*
Li et al. "Limitation of Peptide Retro-inverso Isomerization in Molecular Mimicry", The Journal of Biological Chemistry, 2010, 19572-19581 (Year: 2012).*
International Search Report, PCT/CN2017/114796 [ISA/CN] dated Mar. 13, 2018.
YAO,V.J. et al. "Ligand-Targeted Theranostic Nanomedicines against Cancer", Journal of Controlled Release, vol. 240, Oct. 28, 2016.

* cited by examiner

*Primary Examiner* — Lianko G Garyu
(74) *Attorney, Agent, or Firm* — Edwin S. Flores; Daniel J. Chalker; Chalker Flores, LLP

(57) ABSTRACT

Provided in the present invention are highly stable D-configuration polypeptides DVAP and SVAP having a high binding activity to the GRP78 protein, and also provided are an L-configuration polypeptide LVAP and a DVAP-or SVAP-modified model drug and a macromolecule carrier material, and the use thereof in the construction of a tumour image and a drug-delivery system for targeted treatment.

14 Claims, 19 Drawing Sheets

Specification includes a Sequence Listing.

FIG. 18A
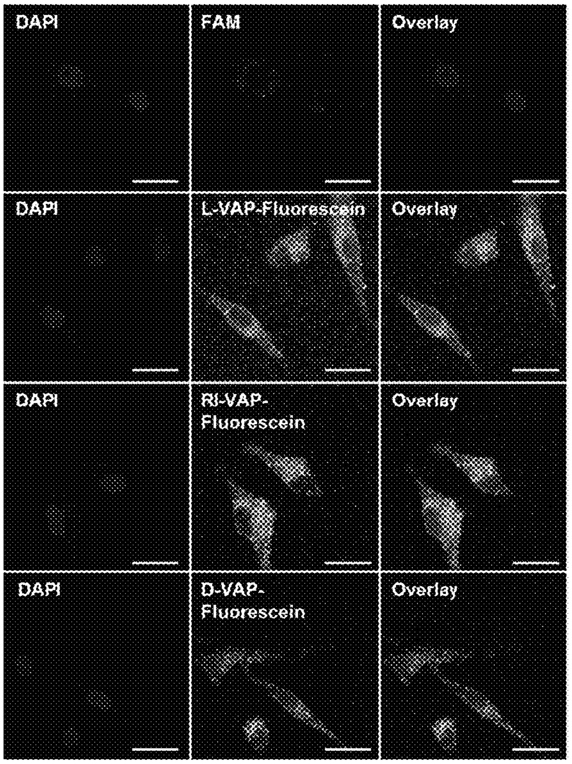
FIG. 18B
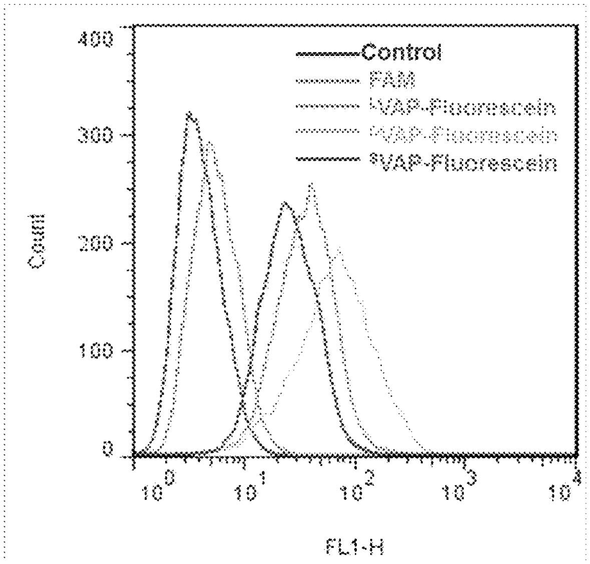
FIGS. 18A-18B

FIG. 19A
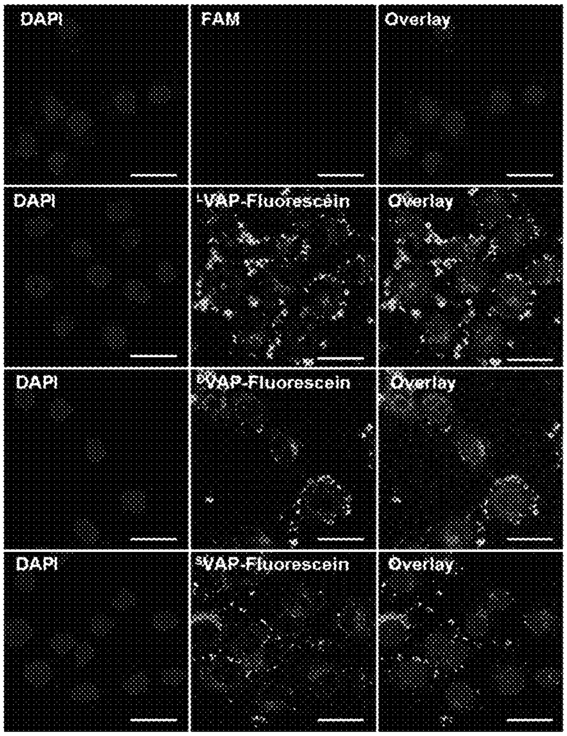
FIG. 19B
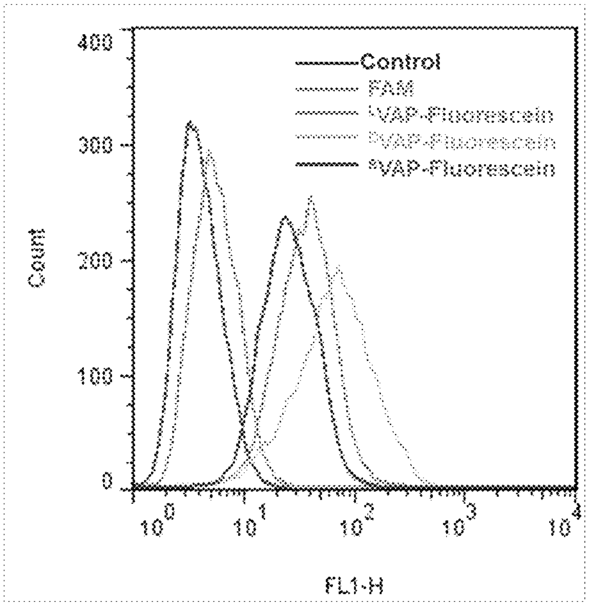
FIGS. 19A-19B

| group | DOX (2.5mg/kg) | Mal-DOX (2.5mg/kg) | RGD-DOX (2.5mg/kg) | VAP-DOX (2.5mg/kg) | Mal-DOX (1.25mg/kg) | VAP-DOX (1.25mg/kg) |
|---|---|---|---|---|---|---|
| Tumor inhibition rate | 49.7% | 64.8% | 85.90% | 94.8% | 65.0% | 85.3% |

A

| Parameters | DOX | VAP-DOX | MAL-DOX |
|---|---|---|---|
| $T_{1/2}$ (h) | 2.131±0.646 | 2.257±0.268 | 1.878±0.263 |
| $AUC_{0-6h}$ (mg/L·h) | 7.976±1.515 | 38.198±5.071 | 154.875±13.290 |
| $MRT_{0-6h}$ (h) | 1.836±0.695 | 2.098±0.137 | 1.903±0.201 |

B

VAP POLYPEPTIDE AND USE THEREOF IN PREPARATION OF DRUG FOR TARGETED DIAGNOSIS AND TREATMENT OF TUMOR

CROSS-REFERENCE TO RELATED APPLICATIONS

This application is the National Stage of International Application No. PCT/CN2017/114796, filed on Dec. 6, 2017 claiming the priority of CN 01611115191.1, filed on Dec. 7, 2016, the content of each of which is incorporated by reference herein.

STATEMENT OF FEDERALLY FUNDED RESEARCH

None.

INCORPORATION-BY-REFERENCE OF MATERIALS FILED ON COMPACT DISC

The present application includes a Sequence Listing, which has been submitted in ASCII format via EFS-Web and is hereby incorporated by reference in its entirety. Said ASCII copy, created on Jul. 9, 2020, is named INNO1005US_SeqList and is 1 kilobytes in size.

The present invention belongs to the field of medicine and relates to VAP peptide and use thereof in preparation of drug, and in particular relates to a multifunctional D-configuration peptide which is highly stable and can target glucose-regulated protein GRP78, drug complex and modified nano drug delivery system of L-configuration peptide and stable D-configuration peptide. In particular, it relates to D-configuration peptides $^{D}$VAP (D-configuration amino acid sequence $^{D}P^{D}A^{D}V^{D}R^{D}T^{D}N^{D}S$) (SEQ ID NO:1) and $^{S}$VAP (D-configuration amino acid sequence $^{D}S^{D}N^{D}T^{D}R^{D}V$-$^{D}A^{D}P$) (SEQ ID NO:2), diagnostic and therapeutic drug complexes of L-configuration peptide $^{L}$VAP (amino acid sequence SNTRVAP (SEQ ID NO:2)) and stable D-configuration peptide, peptide modified polymer carrier materials and nano drug delivery systems constructed by them such as liposomes, polymer micelles, polymer disks, nanoparticles and so on, as well as uses in preparation of drugs for diagnosis and targeted treatment of tumor.

BACKGROUND OF THE INVENTION

The literature reports that tumors are diseases that seriously threaten human life and health, and its mortality is one of the highest among diseases. As the main means of tumor drug therapy, traditional chemotherapy has the defects of poor selectivity to tumor tissue, high toxicity, narrow therapeutic windows and prone to multiple drug resistance and so on. Therefore, in order to overcome these limitations, active targeting has become an important strategy to improve the targeting efficiency of tumor site in recent years. Information disclose that active targeting strategies are mainly realized by ligands' recognition and binding capacity to specific receptors or transporters that are highly expressed in tumor tissues, mediating drugs or nano drug delivery systems to tumor tissues or cells. The corresponding ligands commonly used include monoclonal antibodies, peptides, aptamers, small molecule compounds, and so on; the ligand modified drug or nano drug delivery system can deliver the drug to tumor site and cells through specific recognition, binding and internalization of cell surface receptors or transporters and ligands, thus realizing the active target of the drug to tumors.

Glucose-regulated protein GRP78, also known as immunoglobulin heavy-chain binding protein (Bip), is one of the major molecular chaperones of the endoplasmic reticulum and plays an important role in protein folding and endoplasmic reticulum stress response. Researches have shown that the expression of GRP78 is significantly increased in several tumor cell lines, solid tumors and human cancer tissue biopsy samples. Overexpression of GRP78 protein is evidenced in various tumors such as breast cancer, liver cancer, colon cancer and gastric cancer, and which closely related to the occurrence, progression, prognosis and drug resistance of these tumors. Recent researches have shown that GRP78 can be transferred to the surface of cell membranes in tumor cells, while this phenomena is not observed on normal cells. Researches have also shown that through Cripto/GRP78 signal pathway which regulates the function of adult stem cells and tumor stem cells, GRP78 plays a key role in the regulation of cancer stem cells and maintain their stemness. Therefore, specific delivery of drugs or nano drug delivery systems to tumor site through GRP78 receptor-mediated pathway has enormous value in improving the tumor diagnosis and treatment effects of drugs.

$^{L}$VAP (L-configuration amino acid sequence SNTRVAP (SEQ ID NO:2)) is a heptapeptide selected by phage display technology. It has been proved to have high affinity to GRP78, but the application on tumor diagnosis and targeted treatment has never been reported yet.

Based on the current state of the art, the inventors of the present application intend to provide the application of VAP peptide in the diagnosis and targeted treatment of tumors and further optimize the stability of existing peptides to achieve better tumor targeting effects in vivo.

SUMMARY OF THE INVENTION

Aiming at the defects of the prior art, the purpose of the invention is to provide VAP peptide and its application in tumor diagnosis and targeted treatment, and further optimize the stability of the existing peptide for better tumor targeted effect in vivo.

The first aspect of the present invention provides a D-configuration peptide, the D-configuration peptide is $^{D}$VAP and/or $^{S}$VAP, and the amino acid sequence of the $^{D}$VAP is $^{D}P^{D}A^{D}V^{D}R^{D}T^{D}N^{D}S$, the amino acid sequence of the $^{S}$VAP is $^{D}S^{D}N^{D}T^{D}R^{D}V^{D}A^{D}P$.

The second aspect of the present invention provides a peptide complex of $^{D}$VAP and/or $^{S}$VAP, the $^{D}$VAP and/or $^{S}$VAP peptide complex is maleimide-group-contained imaging substance modified by the $^{D}$VAP and/or $^{S}$VAP of the first aspect, wherein the structure of the $^{D}$VAP and/or $^{S}$VAP peptide complex is $^{D}$VAP-X and/or $^{S}$VAP-X, X is the image substance;

preferably, the X is one or more selected from of the group consisting of fluorescent substance, near-infrared dye, magnetic resonance imaging agent, and radiographic agent;

more preferably, the fluorescent substance is Fluorescein, the near-infrared dye is Cy7, IR820, DiR, the magnetic resonance imaging agent is Gd-DTPA, the radiographic agent is $^{99m}$Tc-DTPA.

The third aspect of the present invention provides a peptide complex of L-configuration peptide $^{L}$VAP, the $^{L}$VAP peptide complex is maleimide-group-contained imaging substance modified by the $^{L}$VAP, wherein the amino acid sequence of the $^{L}$VAP peptide is SNTRVAP (SEQ ID NO:2), and the structure of the $^{L}$VAP peptide complex is $^{L}$VAP-X, X is the image substance;

preferably, the X is one or more selected from of the group consisting of fluorescent substance, near-infrared dye, magnetic resonance imaging agent, and radiographic agent;

more preferably, the fluorescent substance is Fluorescein, the near-infrared dye is Cy7, IR820, DiR, the magnetic resonance imaging agent is Gd-DTPA, the radiographic agent is $^{99m}$Tc-DTPA.

The fourth aspect of the present invention provides a peptide complex of $^{D}$VAP and/or $^{S}$VAP, the $^{D}$VAP and/or $^{S}$VAP peptide complex is antitumor drug modified by the $^{D}$VAP and/or $^{S}$VAP peptide of the first aspect, wherein the structure of the $^{D}$VAP and/or $^{S}$VAP peptide complex is $^{D}$VAP-Y and/or $^{S}$VAP-Y, Y is the antitumor drug;

preferably, the antitumor drug is one or more selected from of the group consisting of anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide, melittin, scorpion venom peptide and antimicrobial peptides;

more preferably, the antitumor drug is one or more selected from of the group consisting of doxorubicin or epirubicin, which contains ketone or aldehyde group; paclitaxel, docetaxel, camptothecin, hydroxycamptothecin, 9-nitro camptothecin, vincristine, etoposide, gemcitabine, cytarabine, 5-fluorouracil, teniposide, moritinib, epothilone, vinorelbine, actinomycin D, mitoxantrone anthraquinone, mitomycin, bleomycin, irinotecan, which containing hydroxyl or amino group; bortezomib or carfilzomib, which containing boric acid and/or one of the peptide drugs of p53 activating peptide, melittin and scorpion venom peptide.

The fifth aspect of the present invention provides a peptide complex of L-configuration peptide $^{L}$VAP, the $^{L}$VAP peptide complex is antitumor drug modified by the $^{L}$VAP, wherein the amino acid sequence of the $^{L}$VAP peptide is SNTRVAP (SEQ ID NO:2), and the structure of the $^{L}$VAP peptide complex is $^{L}$VAP-Y, Y is the antitumor drug;

preferably, the antitumor drug is one or more selected from of the group consisting of anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide and melittin, scorpion venom peptide and antimicrobial peptides;

more preferably, the antitumor drug is one or more selected from of the group consisting of doxorubicin or epirubicin, which contains ketone or aldehyde group; paclitaxel, docetaxel, camptothecin, hydroxycamptothecin, 9-nitro camptothecin, vincristine, etoposide, gemcitabine, cytarabine, 5-fluorouracil, teniposide, moritinib, epothilone, vinorelbine, actinomycin D, mitoxantrone anthraquinone, mitomycin, bleomycin, irinotecan, which containing hydroxyl or amino group; bortezomib, which containing boric acid and/or one of the peptide drugs of p53 activating peptide, melittin and scorpion venom peptide.

The sixth aspect of the present invention provides a peptide complex of $^{D}$VAP and/or $^{S}$VAP, the $^{D}$VAP and/or $^{S}$VAP peptide complex is polymer carrier material modified by the $^{D}$VAP and/or $^{S}$VAP of the first aspect, wherein the structure of the $^{D}$VAP and/or $^{S}$VAP peptide complex is $^{D}$VAP-polyethylene glycol-Z and/or $^{S}$VAP-polyethylene glycol-Z, Z is the polymer carrier material;

preferably, the polymer carrier material is one or more selected from of the group consisting of phospholipids, polylactic acid, poly lactic-co-glycolic acid, and polycaprolactones.

The seventh aspect of the present invention provides a peptide complex of L-configuration $^{L}$VAP, the $^{L}$VAP peptide complex is polymer carrier material modified by the $^{L}$VAP, wherein the amino acid sequence of $^{L}$VAP peptide is SNTRVAP (SEQ ID NO:2), and the structure of the $^{L}$VAP peptide complex is $^{L}$VAP-polyethylene glycol-Z, Z is the polymer carrier material;

preferably, the polymer carrier material is one or more selected from of the group consisting of phospholipids, polylactic acid, poly lactic-co-glycolic acid, and polycaprolactones.

The eighth aspect of the present invention provides a drug delivery system, characterized in that, the drug delivery system comprises the complex of the sixth or seventh aspect;

preferably, the drug delivery system is liposome delivery system, polymer micelle delivery system, polymer disc delivery system or nanoparticle delivery system.

According to the drug delivery system of the eighth aspect, besides the $^{D}$VAP, $^{S}$VAP and/or $^{L}$VAP peptide complex, the drug delivery system further comprises (1) diagnostic drug and/or (2) antitumor drug;

preferably: the (1) diagnostic drug is one or more selected from of the group consisting of fluorescent substance, near-infrared dye and magnetic resonance imaging agent, and more preferably, the fluorescent substance is Fluorescein, the near-infrared dye is selected from Cy7, IR820, DiR, and/or the magnetic resonance imaging agent is Gd-DTPA, and/or the (2) anti-tumor drug is one or more selected from of the group consisting of anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide, melittin, scorpion venom peptide and antimicrobial peptides.

The ninth aspect of the present invention provides the use in the manufacture of drug or medical product for the diagnosing, tracing and/or treating tumor, the $^{D}$VAP and/or $^{S}$VAP peptide of the first aspect, the $^{D}$VAP, $^{S}$VAP and/or $^{L}$VAP peptide complex of any one of the second to the seventh aspect, the drug delivery system of the eighth or ninth aspect, preferably: the tumor is glucose-regulating protein GRP78 high expressed tumor.

The tenth aspect of the present invention provides a method for tumor diagnosis and/or targeted therapy, characterized in that, administering to a subject in need thereof:

D-configuration peptide according to the first aspect;

$^{D}$VAP, $^{S}$VAP and/or $^{L}$VAP peptide complex according to any one of the second to the seventh aspect; and/or drug delivery system of the eighth or ninth aspect.

The stabilized D-configuration VAP peptide of the present invention wherein the D-configuration VAP peptide is $^{D}$VAP and/or $^{S}$VAP, and the amino acid sequence of the $^{D}$VAP is $^{D}P^{D}A^{D}V^{D}R^{D}T^{D}N^{D}S$, and the amino acid sequence of the $^{S}$VAP is $^{D}S^{D}N^{D}T^{D}R^{D}V^{D}A^{D}P$.

Specifically, the present invention designs and prepares D-configuration peptide $^{D}$VAP and/or $^{S}$VAP, both peptides have high stability to serum and high affinity to GRP78.

The complex of D-configuration peptide in the present invention or the L-configuration peptide ($^{L}$VAP, amino acid sequence is SNTRVAP (SEQ ID NO:2)) reported in the literature, the $^{D}$VAP, $^{S}$VAP, $^{L}$VAP peptide complex is image substances modified by $^{D}$VAP, $^{S}$VAP, $^{L}$VAP, and wherein the structure of the $^{D}$VAP, $^{S}$VAP, $^{L}$VAP peptide complex is $^{D}$VAP-X, $^{S}$VAP-X and/or $^{L}$VAP-X, wherein X is the image substance.

Preferably, the X is one or more selected from of the group consisting of fluorescein, near-infrared dye, magnetic resonance imaging agent and radiographic agent. More preferably, the fluorescein is Fluorescein, and the near-infrared dye is one or more selected from of the group consisting of cy7, IR820 and DiR; the magnetic resonance imaging agent is Gd-DTPA, and the radiographic imaging agent is $^{99m}$Tc-DTPA.

Specifically, after sulfhydrylated, $^{D}$VAP, $^{S}$VAP of the present invention or the $^{L}$VAP reported in the literature can utilize the sulfhydryl group in the molecule to react with the maleimide functionalized fluorescent substances (such as Fluorescein, near-infrared dye cy7, IR820, DiR, etc.), maleimide functionalized magnetic resonance imaging agent Gd-DTPA and maleimide functionalized radiographic imaging agent $^{99m}$Tc-DTPA to form the complex.

The complex of $^{D}$VAP, $^{S}$VAP of the present invention or the $^{L}$VAP reported in the literature, the $^{D}$VAP, $^{S}$VAP, $^{L}$VAP peptide complex is antitumor drug modified by $^{D}$VAP, $^{S}$VAP, $^{L}$VAP, and wherein the structure of the $^{D}$VAP, $^{S}$VAP, $^{L}$VAP peptide complex is $^{D}$VAP-Y, $^{S}$VAP-Y and/or $^{L}$VAP-Y, wherein Y is antitumor drug.

Preferably, the antitumor drug is one or more selected from of the group consisting of anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide, melittin, scorpion venom peptide and antimicrobial peptides.

More preferably, the antitumor drug is one or more selected from of the group consisting of doxorubicin or epirubicin, which contains ketone or aldehyde group; paclitaxel, docetaxel, camptothecin, hydroxycamptothecin, 9-nitro camptothecin, vincristine, etoposide, gemcitabine, cytarabine, 5-fluorouracil, teniposide, moritinib, epothilone, vinorelbine, actinomycin D, mitoxantrone Anthraquinone, mitomycin, bleomycin, irinotecan, which containing hydroxyl or amino; bortezomib or carfilzomib, which containing boric acid group; and/or the peptide drugs of p53 activating peptide, melittin and scorpion venom peptide.

Specifically, the drugs modified by $^{D}$VAP, $^{S}$VAP of the present invention or the $^{L}$VAP reported in the literature, including peptide-drug complexes that form pH-sensitive hydrazone bonds by the reaction of maleimidohydrazine derivative (involving doxorubicin or epirubicin and other drugs containing ketone or aldehyde group), or peptide-drug complexes that form di sulfide bonds by the reaction of 3-(2-pyridyldithio) propionic acid derivative (involving paclitaxel, docetaxel, camptothecin, hydroxycamptothecin, 9-nitro camptothecin, vincristine, etoposide, gemcitabine, cytarabine, 5-fluorouracil, teniposide, moritinib, epothilone, vinorelbine, actinomycin D, mitoxantrone Anthraquinone, mitomycin, bleomycin, irinotecan, and other drugs containing hydroxyl or amino group), or peptide-drug complexes that form pH-sensitive boric acid esters by reaction of dopamine and boric acid group of the drugs (involving bortezomib and other drugs containing boric acid), or peptide-drug complexes that form amide bond directly by solid phase synthesis (involving p53 activating peptide, antimicrobial peptide, peptide toxin and other peptide drugs).

The complex of $^{D}$VAP, $^{S}$VAP of the present invention or the $^{L}$VAP reported in the literature, the $^{D}$VAP, $^{S}$VAP, $^{L}$VAP peptide complex is polymer materials modified by $^{D}$VAP, $^{S}$VAP, $^{L}$VAP, and wherein the structure of the $^{D}$VAP, $^{S}$VAP, $^{L}$VAP peptide complex is $^{D}$VAP-polyethylene glycol-Z, $^{S}$VAP-polyethylene glycol-Z and/or $^{L}$VAP-polyethylene glycol-Z, wherein Z is polymer carrier materials.

Preferably, the polymer carrier material is one or more selected from of the group consisting of phospholipids, polylactic acid, poly lactic-co-glycolic acid, and polycaprolactones.

Specifically, after sulfhydrylated, $^{D}$VAP, $^{S}$VAP of the present invention or the $^{L}$VAP reported in the literature can modify polymer carrier materials containing maleimide functional groups such as polyethylene glycol-distearoyl phosphoethanolamine (PEG-DSPE), polyethylene glycol-polylactic acid (PEG-PLA), polyethylene glycol-poly lactic-co-glycolic acid (PEG-PLGA), polyethylene glycol-polycaprolactone (PEG-PCL), which can be used in the construction of nano drug delivery systems such as $^{D}$VAP, $^{S}$VAP, $^{L}$VAP modified liposomes, polymer micelles, polymer disks, and nanoparticles.

The drug delivery system of the present invention, the drug delivery system comprises the aforementioned $^{D}$VAP, $^{S}$VAP, $^{L}$VAP peptide complex. Preferably, the drug delivery system is liposome drug delivery system, polymer micelle drug delivery system, polymer disk drug delivery system, and nanoparticle drug delivery system.

As preferred embodiment, the present invention also provides aforementioned drug delivery system include (1) diagnostic drug and/or (2) antitumor drug besides the $^{D}$VAP, $^{S}$VAP, $^{L}$VAP peptide complex.

Preferably, the (1) diagnostic drug is one or more selected from of the group consisting of fluorescent substance, near-infrared dye, and magnetic resonance imaging agent. More preferably, the fluorescent substance is Fluorescein, the near-infrared dye is one or more selected from of the group consisting of Cy7, IR820, DiR, and/or the magnetic resonance imaging agent is Gd-DTPA. And/or the (2) antitumor drug is one or more selected from of the group consisting of anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide, melittin, scorpion venom peptide and antimicrobial peptides.

Specifically, the nano drug delivery system modified by $^{D}$VAP, $^{S}$VAP $^{L}$VAP designed by the present invention can encapsulate anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide, melittin, scorpion venom peptide and antimicrobial peptides and so on; and it can also encapsulate fluorescent substance, near-infrared dye, and magnetic resonance imaging agent such as Fluorescein, Cy7, IR820, Di, Gd-DTPA and so on.

The present invention also provides the use of the aforementioned peptide of $^{D}$VAP, $^{S}$VAP, the aforementioned peptide complex of $^{D}$VAP, $^{S}$VAP, $^{L}$VAP, the aforementioned drug delivery system in the preparation of drugs or medical products for diagnosing, tracing or treating tumors.

Preferably, The tumor is GRP78 high expressed tumor.

Specifically, the $^{D}$VAP, $^{S}$VAP of the first aspect of the present invention or the $^{L}$VAP reported in the literature can mediate drug or nano drug delivery system targeting GRP78 high expressed cells and tissues for diagnosis and targeted treatment of tumor.

The present invention also provides a combination product for diagnosing, tracing, and/or treating tumor, the combination product comprising one or more components selected from of the group consisting of the aforementioned $^{D}$VAP, $^{S}$VAP, $^{L}$VAP peptide complex and the aforementioned drug delivery system.

Preferably, the combination product is a kit, and/or

The tumor is GRP78 high expressed tumor.

A method for diagnosing, tracing, and/or treating tumor of the present invention, comprising administering via an oral or non-oral route to a patient an effective amount of one or more substance selected from: the aforementioned $^{D}$VAP, $^{S}$VAP, $^{L}$VAP peptide complexes, the aforementioned drug delivery systems, and the aforementioned combinations.

Preferably, the tumor is GRP78 high expressed tumor; and/or preferably, the oral or non-oral route can be one or more of oral, injection, patch, spray, and other known route delivered to the patient. The effective amount can include an amount effective to treat, reduce, ease, alleviate, eliminate condition of one or more symptoms, the condition is sought to be treated, or alternatively, the condition is sought to be avoided, or otherwise clinically identifiable favorable change occur in the condition or its effect.

The present invention provides the use of aforementioned peptide of $^{D}$VAP, $^{S}$VAP, $^{L}$VAP in the preparation of tumor targeting products. Preferably: the tumor targeting product is for targeting tumor with high expression of GRP78; and/or the tumor targeting product is drug, experimental reagent and/or medical product for diagnosing, tracing and/or treating tumor. The present invention provides $^{L}$VAP peptide (SNTRVAP (SEQ ID NO:1)) modified drug complex and nano drug delivery system; and aiming at the problem that L-configuration peptide has poor stability in vivo and is easily degraded in blood that may result in the decreasing of tumor targeting ability, the present invention provides D-configuration peptide targeting molecule $^{D}$VAP (D-configuration amino acid sequence $^{D}$P$^{D}$A$^{D}$V$^{D}$R$^{D}$T$^{D}$N $^{D}$S (SEQ ID NO:1)) and $^{S}$VAP (D-configuration amino acid sequence $^{D}$S$^{D}$N$^{D}$T$^{D}$R$^{D}$V$^{D}$A$^{D}$P (SEQ ID NO:2)) with high stability and high affinity to GRP78, and to construct its drug complex and modified nano drug delivery system, which can achieve diagnosis and targeted treatment of tumors, and obtain better tumor targeting effects in vivo.

Specifically, the present invention prepares D-configuration peptide targeting molecule D-configuration peptides $^{D}$VAP (D-configuration amino acid sequence $^{D}$P$^{D}$A$^{D}$V$^{D}$R$^{D}$T$^{D}$N$^{D}$S(SEQ ID NO:1)) and $^{S}$VAP (D-configuration amino acid sequence $^{D}$S$^{D}$N$^{D}$T$^{D}$R $^{D}$V$^{D}$A$^{D}$ P (SEQ ID NO:2)) with high stability, and modifies drug molecule or polymer carrier material by $^{L}$VAP (L-configuration amino acid sequence SNTRVAP (SEQ ID NO:1)), $^{D}$VAP and $^{S}$VAP to build VAP drug complex and VAP modified nano drug delivery system.

In the present invention, D-configuration peptide targeting molecule $^{D}$VAP (D-configuration amino acid sequence $^{D}$P$^{D}$A$^{D}$V$^{D}$R$^{D}$T$^{D}$N$^{D}$S) and $^{S}$VAP (D-configuration amino acid sequence $^{D}$S$^{D}$N$^{D}$T$^{D}$R$^{D}$V$^{D}$A$^{D}$P) is designed and prepared by solid phase polypeptide synthesis technology, and both peptides have high stability to serum and high affinity to GRP78.

In the present invention, after linked with cysteine, the $^{L}$VAP or $^{D}$VAP, $^{S}$VAP as designed can form complex by reacting sulfhydryl in the molecule with maleimide functional imaging substances (fluorescein substances such as Fluorescein, near infrared dyes such as Cy7, IR820, DiR, magnetic resonance imaging agent such as Gd-DTPA, radiographic imaging agent such as $^{99m}$Tc-DTPA, etc.).

In the present invention, the $^{L}$VAP or $^{D}$VAP, $^{S}$VAP as designed can modify drugs, which include peptide drug complexes that form pH-sensitive hydrazone bonds by the reaction of maleimidohydrazine derivative (involving doxorubicin or epirubicin and other drugs containing ketone or aldehyde groups), or peptide drug complexes that form disulfide bonds by the reaction of 3-(2-pyridyldithio)propionic acid derivative (involving paclitaxel, docetaxel, camptothecin, hydroxycamptothecin, 9-nitro camptothecin, vincristine, etoposide, gemcitabine, cytarabine, 5-fluorouracil, teniposide, moritinib, epothilone, vinorelbine, actinomycin D, mitoxantrone Anthraquinone, mitomycin, bleomycin, irinotecan, and other drugs containing hydroxyl or amino), or peptide drug complexes that form pH-sensitive boric acid esters by reaction of dopamine and boric acid groups in the drugs (involving bortezomib and other drugs containing boric acid), or peptide drug complexes that form amide bond directly by solid phase synthesis (involving p53 activating peptide, antimicrobial peptide, peptide toxin and other peptide drugs).

In the present invention, after linked with cysteine, $^{D}$VAP, $^{S}$VAP of the present invention or the $^{L}$VAP reported in the literature can modify polymer carrier materials containing maleimide functional group such as polyethylene glycol-distearoyl phosphoethanolamine (PEG-DSPE), polyethylene glycol-polylactic acid (PEG-PLA), polyethylene glycol-poly lactic-co-glycolic acid (PEG-PLGA), polyethylene glycol-polycaprolactone (PEG-PCL), which can be used in the construction of nano drug delivery systems such as liposomes, polymer micelles, polymer disks, and nanoparticles modified by $^{D}$VAP, $^{S}$VAP, $^{L}$VAP.

In the present invention, the nano drug delivery system modified by $^{D}$VAP, $^{S}$VAP, $^{L}$VAP encapsulate anthracyclines such as doxorubicin or epirubicin, taxanes such as taxol and docetaxel and cabazitaxel, camptothecins such as camptothecin and hydroxycamptothecin and irinotecan, vinblastines such as vincristine and vinorelbine, proteasome inhibitors such as bortezomib and carfilzomib, lactones such as parthenolide, peptide drugs such as p53 activating peptide and melittin, scorpion venom peptide and antimicrobial peptides and so on. Or it can also encapsulate imaging substances, such as Fluorescein, near-infrared dye such as Cy7, IR820, DiR, magnetic resonance imaging agent Gd-DTPA and so on.

The $^{D}$VAP, $^{S}$VAP and $^{L}$VAP of the present invention can mediate drugs or nano drug delivery systems targeting cells and tissues with high expression of the glucose-regulating protein GRP78 for diagnosis and targeted treatment of tumors.

The present invention provides preparation and property investigation for $^{D}$VAP and $^{S}$VAP and substance basis for that above-mentioned $^{L}$VAP, $^{D}$VAP and $^{S}$VAP modified drug complexes and nano drug delivery systems for preparing tumor diagnosis and treatment drugs; and carries out experiments of $^{L}$VAP, $^{D}$VAP, and $^{S}$VAP-mediated active targeting in vivo, which including:

1. Synthesis of VAP, VAP-Cys and their Fluorescent Derivatives (VAP-Fluorescein, VAP-Cy7)

$^{L}$VAP, $^{L}$VAP-Cys, $^{D}$VAP, $^{D}$VAP-Cys, $^{S}$VAP, $^{S}$VAP-Cys were prepared by solid phase synthesis. $^{L}$VAP-Fluorescein, $^{D}$VAP-Fluorescein, $^{S}$VAP-Fluorescein, $^{L}$VAP-Cy7, $^{D}$VAP-Cy7, $^{S}$VAP-Cy7 were synthesized by Michael addition reaction of maleimide group with sulfhydryl group. The products were characterized by HPLC and MS.

2. VAP Stability and Receptor Affinity Evaluation

Serum stability, binding capacity to glucose-regulated protein GRP78, and cellular uptake by GRP78 high expressed cells of $^{D}$VAP and $^{S}$VAP were examined: $^{D}$VAP, $^{S}$VAP and $^{L}$VAP were incubated with mouse serum at 37° C. respectively, and the concentration of peptide was measured at different time points for stability comparison. The surface plasmon resonance method was used to evaluate the binding capacity of $^{D}$VAP, $^{S}$VAP and $^{L}$VAP to GRP78, and in vitro targeting ability of GRP78 high expressed cells (e.g. human umbilical vein endothelial cells HUVEC) and model tumor cells (e.g. glioma cell U87) was compared and the intake capacity of in vitro 3D tumor spheroid models to $^{D}$VAP-Fluorescein, $^{S}$VAP -Fluorescein, $^{L}$VAP-Fluorescein was compared.

3. Preparation of VAP Drug Complex

After linked with cysteine, $^{L}$VAP, $^{D}$VAP and $^{S}$VAP react with maleimidohydrazine derivative of the drug to form peptide drug complex containing a pH-sensitive hydrazone bond. The drug involved includes drugs containing ketone or aldehyde group such as doxorubicin and epirubicin and so on;

After linked with cysteine, $^{L}$VAP, $^{D}$VAP and $^{S}$VAP react with the 3-(2-pyridyldithio)propionic acid derivative of the drug to form peptide drug complex containing disulfide bond. The drug involved includes paclitaxel, docetaxel, camptothecin, hydroxycamptothecin, 9-nitrocamptothecin, vincristine and so on which containing hydroxyl group or amino group;

After linked with dopamine, $^{L}$VAP, $^{D}$VAP and $^{S}$VAP react with boric acid group of the drug to form peptide drug complex containing pH-sensitive borate, wherein the drug involved includes drugs containing boric acid group such as bortezomib and so on;

$^{L}$VAP, $^{D}$VAP and $^{S}$VAP are directly condensed with peptide drugs by solid phase synthesis to form fusion peptide, and the drugs involved include peptide drugs such as p53 activating peptide, antimicrobial peptide, peptide toxin and so on.

4. In Vivo Pharmacodynamics and Pharmacokinetics of VAP-Doxorubicin Complex

After linked with cysteine, $^{D}$VAP condensed with doxorubicin maleimidohydrazine derivative (MAL-DOX) to form $^{D}$VAP-doxorubicin complex ($^{D}$VAP-DOX). The drug was administered via tail vein in nude mice model bearing U87 subcutaneous transplanted tumor, and anti-tumor effect was evaluated by the tumor volume, tumor weight and tumor inhibition rate. The drug was administered via tail vein in nude mice model bearing U87 intracranial transplanted tumor, and the median survival time was used as an index to evaluate its anti-tumor effect in vivo. The pharmacokinetic curve and distribution in vivo were investigated by fluorescence method after intravenous injection in mice tail.

5. Construction and Characterization of VAP-PEG-PLA Micelle Delivery System

First, $^{L}$VAP, $^{D}$VAP and $^{S}$VAP modified polymeric materials $^{L}$VAP-PEG-PLA, $^{D}$VAP-PEG-PLA and $^{S}$VAP-PEG-PLA were synthesized. The synthesis of the material is achieved by the reaction of the free sulfhydryl group on the cysteine-linked peptide with the maleimide group in the Mal-PEG-PLA. The Mal-PEG-PLA was dissolved in acetonitrile, rotary evaporated to form thin film, then peptide contained PBS (pH 8.0) was added to prepare $^{L}$VAP-PEG-PLA, $^{D}$VAP -PEG-PLA and $^{S}$VAP-PEG-PLA.

Then $^{L}$VAP, $^{D}$VAP and $^{S}$VAP modified micelles ($^{L}$VAP-Micelle, $^{D}$VAP-Micelle, $^{S}$VAP-Micelle) were prepared separately. Micelles were prepared with a certain amount of VAP-PEG-PLA, mPEG-PLA and drugs (coumarin C6, DiR or paclitaxel) by film forming method, and characterized by dynamic light scattering (DLS) to ensure the average size and polydispersity index (PDI).

6. In Vitro and In Vivo Tumor Targeting Evaluation of VAP-Micelle

The uptake of $^{L}$VAP-Micelle/C6, $^{D}$VAP-Micelle/C6, $^{S}$VAP-Micelle/C6 and mPEG-Micelle/C6 in U87 cells, HUVEC cells and U87 tumor spheroids in vitro was investigated.

$^{L}$VAP-Micelle/DiR, $^{D}$VAP-Micelle/DiR, $^{S}$VAP-Micelle/DiR and mPEG-Micelle/DiR were administrated via tail vein in nude mice model bearing U87 subcutaneous transplanted tumor, and intratumoral distribution of different groups at each time point was compared.

7. Evaluation of In Vivo Anti-Tumor Effect of VAP-Micelle/PTX $^{L}$VAP-Micelle/PTX, $^{S}$VAP-Micelle/PTX, $^{D}$VAP-Micelle/PTX and mPEG-Micelle/PTX, clinical preparations of taxol and saline were administrated via vein in nude mice model bearing U87 subcutaneous transplanted tumor, and the anti-tumor effect in vivo of different paclitaxel formulations was evaluated by tumor volume, tumor weight, tumor cell apoptosis, the number of neovascularization and vasculogenic mimicry.

The present invention provides preparation and property investigation for $^{D}$VAP and $^{S}$VAP and substance basis for that above-mentioned $^{L}$VAP, $^{D}$VAP and $^{S}$VAP modified drug complexes and nano drug delivery systems for preparing tumor diagnosis and treatment drugs. The experimental results of the present invention indicate that: $^{L}$VAP, $^{D}$VAP and $^{S}$VAP can all mediate active tumor targeting in vivo; compared with $^{L}$VAP, $^{D}$VAP and $^{S}$VAP has better stability, and thus they achieved better active tumor targeting effect in vivo.

BRIEF DESCRIPTION OF THE DRAWINGS

For a more complete understanding of the features and advantages of the present invention, reference is now made to the detailed description of the invention along with the accompanying figures and in which:

FIGS. 18A and 18B show the uptake of Fluorescein-labeled peptide by glioma cell U87: FIGS. 18A and 18B show the laser confocal photographs and flow cytometry detection results of Fluorescein-labeled $^{D}$VAP, $^{S}$VAP and $^{L}$VAP interacting with U87 cells for 4 h. It shows that the uptake of $^{D}$VAP, $^{S}$VAP and $^{L}$VAP by U87 cells is significantly higher than that of free fluorescein, and there is no significant difference in the uptake of $^{D}$VAP and $^{S}$VAP, which is slightly weaker than $^{L}$VAP.

FIGS. 19A and 19B show the uptake of Fluorescein-labeled peptide by HUVECs (Human Umbilical Vein Endothelial Cells): FIGS. 19A and 19B show the laser confocal photographs and flow cytometry detection results of Fluorescein-labeled $^{D}$VAP, $^{S}$VAP and $^{L}$VAP interacting with HUVEC cells for 4 h. It shows that the uptake of $^{D}$VAP, $^{S}$VAP and $^{L}$VAP by HUVEC cells is significantly higher than that of free fluorescein, and there is no significant difference in the uptake of $^{D}$VAP and $^{S}$VAP, which is slightly weaker than $^{L}$VAP.

FIG. 22A shows ex vivo fluorescence images in tumor after injection of Cy7-labeled peptide for 1 hour in nude mice bearing U87 subcutaneous transplant tumor. FIG. 22B shows the fluorescence semi-quantitative results of each time points after administration. FIG. 22C shows the ex vivo fluorescence images in tumors and organs. FIG. 22D is the ex vivo semi-quantitative analysis of fluorescence intensity in tumor. The accumulation of Cy7-labeled $^{D}$VAP, $^{S}$VAP and $^{L}$VAP in tumors was significantly higher than that of free Cy7 (***$p<0.001$), and the tumor targeting effect is: $^{D}$VAP≈$^{S}$VAP>$^{L}$VAP.

FIG. 23A is curves showing the variation of tumor volume of each group in nude mice according to time. Compared with the saline group, each group of the administration inhibited tumor growth. At the same Dox dose, the effect of $^{D}$VAP-DOX was significantly better than that of DOX and MAL-DOX, and obviously better than that of RGD-DOX. FIG. 23B shows the result of weight and statistical analysis after the nude mice are sacrificed and tumor tissues are taken out. FIG. 23C is photograph of ex vivo tumor tissue. It can be seen that the tumor size and tumor weight of $^{D}$VAP-DOX group were significantly lower than that of the other groups at the same Dox dose.

FIG. 25A shows the pharmacokinetic curve, and FIG. 25B shows the distribution in major organs of mice. The results showed that the AUC of $^{D}$VAP-DOX was significantly lower than that of MAL-DOX, but it was significantly higher than that of free DOX. Moreover, from the distribution in major organs in vivo, $^{D}$VAP-DOX can significantly reduce the distribution of drugs in the heart, which may reduce the side effects of doxorubicin on the heart.

FIG. 26A shows the in vivo fluorescence image after 24 hours of tail vein injection. From left to right is PBS group, mPEG-Micelle/DiR group, $^{L}$VAP-Micelle/DiR group, $^{D}$VAP-Micelle/DiR group and $^{S}$VAP-Micelle/DiR group. FIG. 26B is the fluorescence image of organs. The results indicate that $^{D}$VAP or $^{S}$VAP modified micelles targeted to the tumor site more effectively.

FIGS. 28A and 28B show the inhibition curves of mPEG-Micelle/PTX, $^{D}$VAP-Micelle/PTX, $^{S}$VAP-Micelle/PTX, $^{L}$VAP-Micelle/PTX and Taxol against U87 cells and HUVEC cells, respectively. FIG. 28A shows that the $IC_{50}$ of mPEG-Micelle/PTX, $^{D}$VAP-Micelle/PTX, $^{S}$VAP-Micelle/PTX, $^{L}$VAP-Micelle/PTX and Taxol against U87 cells are 0.73, 0.09, 0.12, 0.59 and 0.75 μM after administered for 4 h and cultured for 72 h. All micelles can inhibit the growth of U87 cells in vitro. The activity of $^{D}$VAP-Micelle/PTX and $^{S}$VAP-Micelle/PTX were 6.56 and 4.92 folds as much as that of $^{L}$VAP-Micelle/PTX respectively. FIG. 28B shows that the $IC_{50}$ of mPEG-Micelle/PTX, $^{D}$VAP-Micelle/PTX, $^{S}$VAP-Micelle/PTX, $^{L}$VAP-Micelle/PTX and Taxol against HUVEC cells were 0.52, 0.04, 0.04, 0.23 and 0.74 μM after administered for 4 h and cultured for 72 h. All micelles can inhibit the growth of HUVEC cells in vitro. The activity of $^{D}$VAP-Micelle/PTX and $^{S}$VAP-Micelle/PTX were 5.75 folds as much as that of $^{L}$VAP-Micelle/PTX.

FIG. 31A is curves showing the tumor volume change with time of each group in nude mice, each of the administration groups inhibited tumor growth. $^{D}$VAP-Micelle/PTX and $^{S}$VAP-Micelle/PTX are remarkable different from $^{L}$VAP-Micelle/PTX (n=8, *p<0.001). After the nude mice sacrificed, the harvested tumors were weighed and statistically analyzed (FIG. 31B). The tumor weights of the $^{D}$VAP-Micelle/PTX and $^{S}$VAP-Micelle/PTX groups were significantly lower than those of $^{L}$VAP-Micelle/PTX (n=8, *p<0.001).

DETAILED DESCRIPTION OF THE INVENTION

Figure 1:
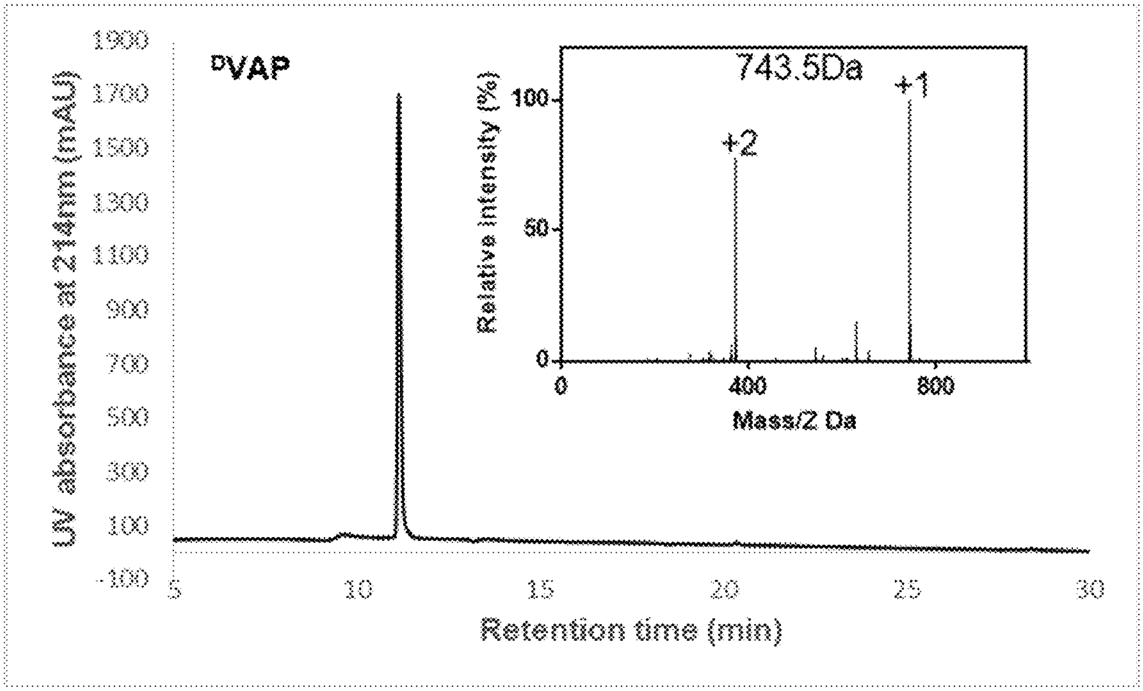
FIG. 1 shows the HPLC and ESI-MS spectra of $^{D}$VAP: Chromatography method: column (YMC, C18): 150×4.6 mm; mobile phase A: water (containing 0.1% trifluoroacetic acid), mobile phase B: acetonitrile (containing 0.1% trifluoroacetic acid); elution procedure: 0-30 min 5% B-65% B; flow rate: 0.7 mL/min; column temperature: 40° C.; detection: UV 214 nm, retention time: 11.1 min. ESI-MS: 743.5, in accordance with the theoretical molecular weight.
Figure 2:
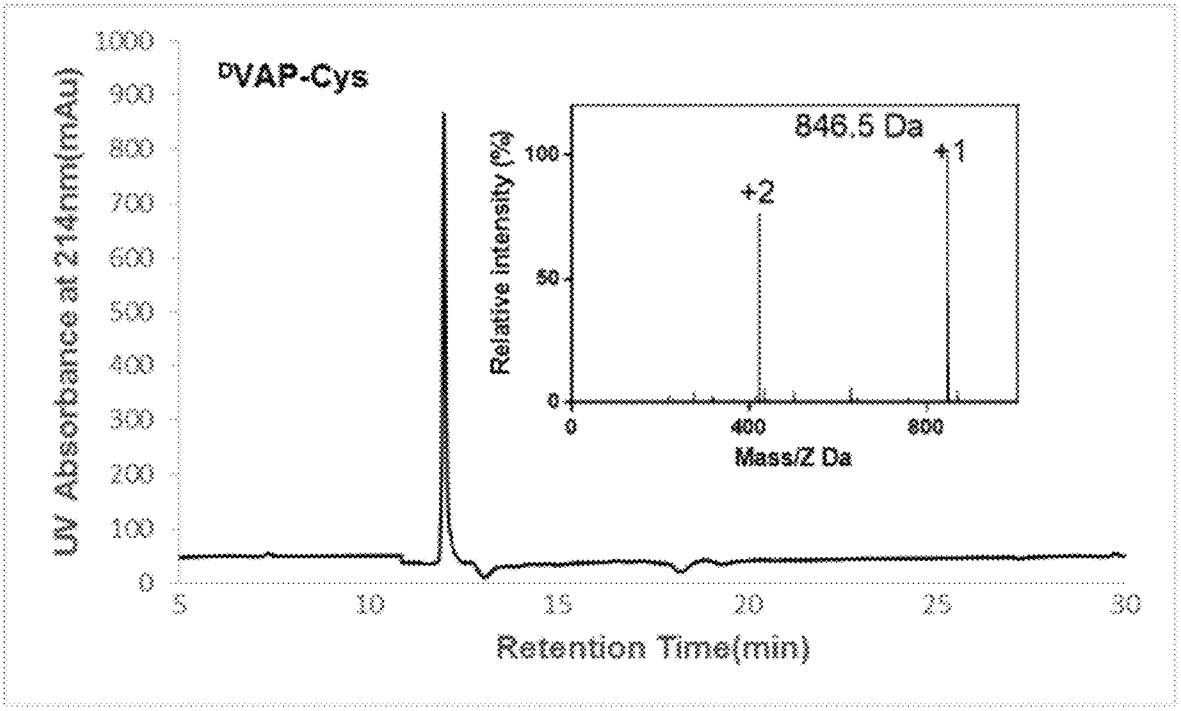
FIG. 2 shows the HPLC and ESI-MS spectra of $^{D}$VAP-Cys: The chromatographic method was the same as above, and the retention time was 12.0 min. ESI-MS: 846.5, in accordance with the theoretical molecular weight.
Figure 3:
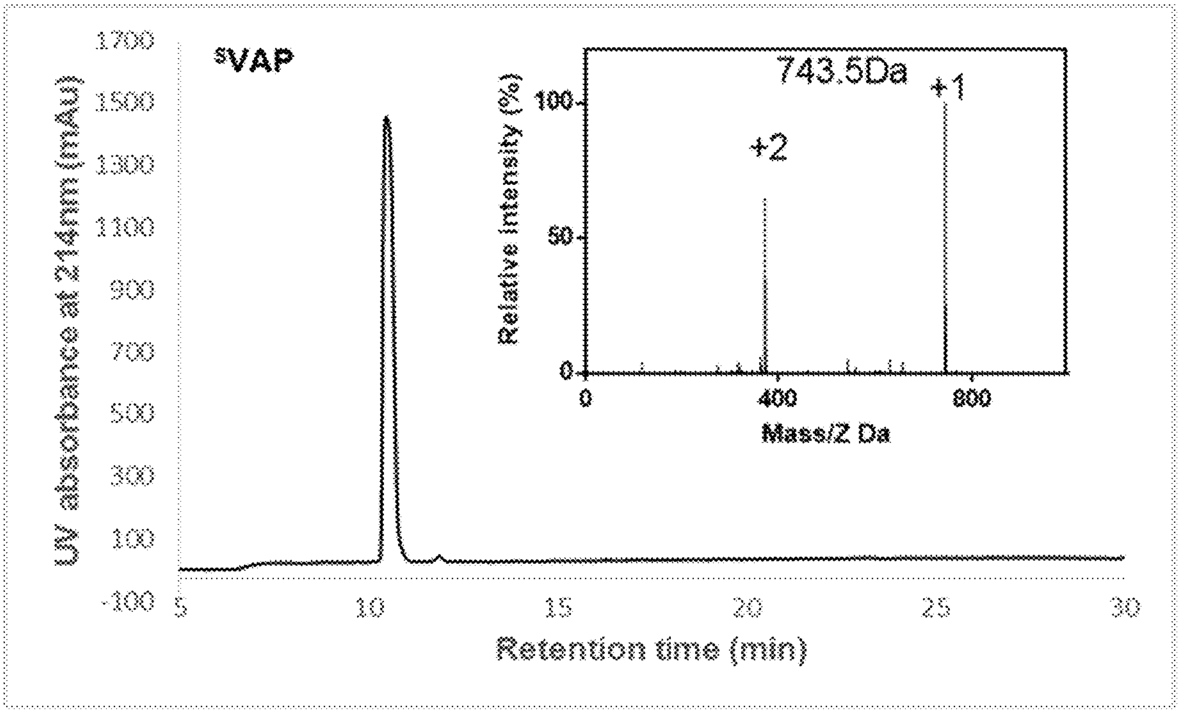
FIG. 3 shows the HPLC and ESI-MS spectra of $^{S}$VAP: The chromatographic method was the same as above, and the retention time was 10.8 min. ESI-MS: 743.5, in accordance with the theoretical molecular weight.
Figure 4:
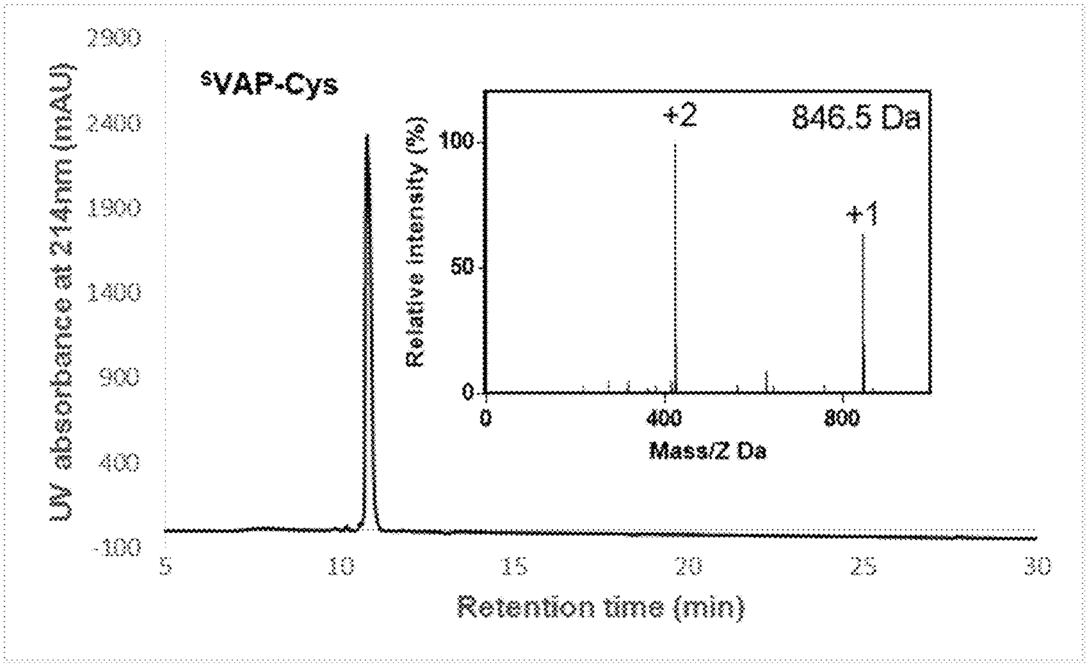
FIG. 4 shows the HPLC and ESI-MS spectra of $^{S}$VAP-Cys: The chromatographic method was the same as above, and the retention time was 11.5 min. ESI-MS: 846.5, in accordance with the theoretical molecular weight.
Figure 5:
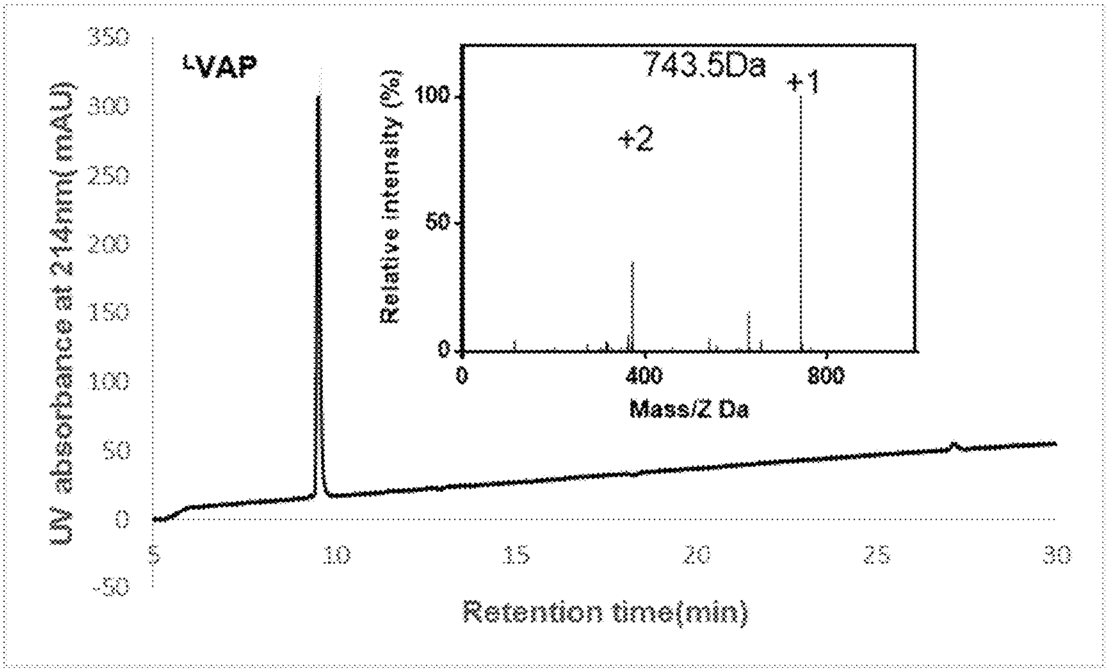
FIG. 5 shows the HPLC and ESI-MS spectra of $^{L}$VAP: The chromatographic method was the same as above, and the retention time was 9.5 min. ESI-MS: 743.5, in accordance with the theoretical molecular weight.
Figure 6:
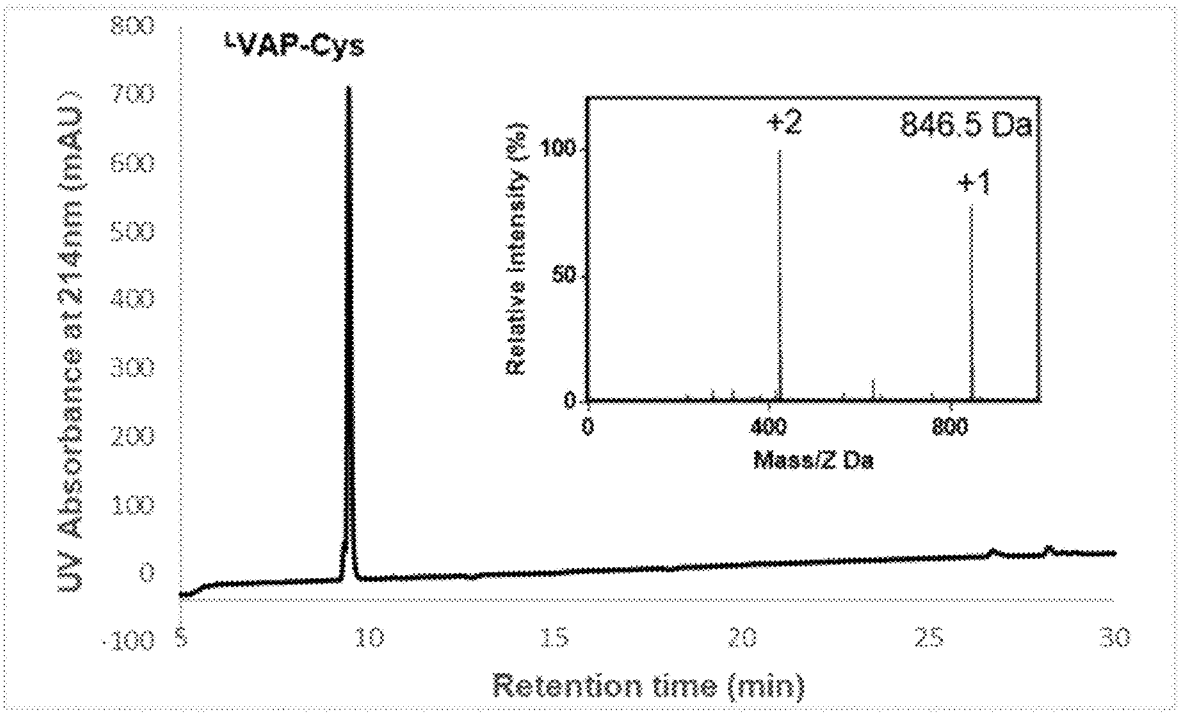
FIG. 6 shows the HPLC and ESI-MS spectra of $^{L}$VAP-Cys: The chromatographic method was the same as above, and the retention time was 9.6 min. ESI-MS: 846.5, in accordance with the theoretical molecular weight.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The invention will be further understood by the following examples, but the invention is not limited to the scope of the following description.

EXAMPLE 1

Synthesis and Characterization of VAP, VAP-Fluorescein, VAP-Cy7, VAP-Drug, VAP-PEG-PLA 1. Synthesis and Characterization of $^{D}$VAP, $^{S}$VAP and $^{L}$VAP, $^{D}$VAP-Cys, $^{S}$VAP-Cys and $^{L}$VAP-Cys Designed $^{D}$VAP (sequence $^{D}$P$^{D}$A$^{D}$V$^{D}$R$^{D}$T$^{D}$N$^{D}$S) (SEQ ID NO:1), $^{D}$VAP-Cys (sequence $^{D}$C$^{D}$P$^{D}$A$^{D}$V$^{D}$R$^{D}$T$^{D}$N$^{D}$S) (SEQ ID NO:4) and $^{S}$VAP (sequence $^{D}$S$^{D}$N$^{D}$T$^{D}$R$^{D}$V$^{D}$A$^{D}$P) (SEQ ID NO:1)), $^{S}$VAP-Cys (squence $^{D}$S$^{D}$N$^{D}$T$^{D}$R$^{D}$V-$^{D}$A$^{D}$P$^{D}$C (SEQ ID NO:5)) composed of D-configuration amino acids and $^{L}$VAP (sequence SNTRVAP (SEQ ID NO:2)) and $^{L}$VAP-Cys (sequence SNTRVAPC (SEQ ID NO:5)) composed of L-configuration amino acids were synthesized by solid phase peptide synthesis.

Specific method: According to the standard Boc-based solid phase peptide synthesis method, Amino acids were sequentially coupled to PAM resin, and the reaction was carried out by using HBTU/DIEA as condensing agent and TFA as deprotecting agent. After all amino acids coupled, the resin was cleavaged by hydrogen fluoride containing P-cresol and stirred in ice bath for 1 hour. The hydrogen fluoride was removed under reduced pressure, and the precipitate was formed and washed three times with ice diethyl ether. The precipitate was redissolved in 20% acetonitrile, and the filtrate was collected and then rotary evaporated to obtain crude peptide solution. The crude peptide was purified by preparative HPLC with acetonitrile/water (containing 0.1% TFA) as eluent. The purity and molecular weight (Mw) of $^{D}$VAP, $^{D}$VAP-Cys, $^{S}$VAP, $^{S}$VAP-Cys, $^{L}$VAP and $^{L}$VAP-Cys were characterized by HPLC and ESI-MS. HPLC spectra and mass spectra are shown in FIGS. 1, 2, 3, 4, 5 and 6.

2. Synthesis and Characterization of VAP-Fluorescein and VAP-Cy7

Figure 7:
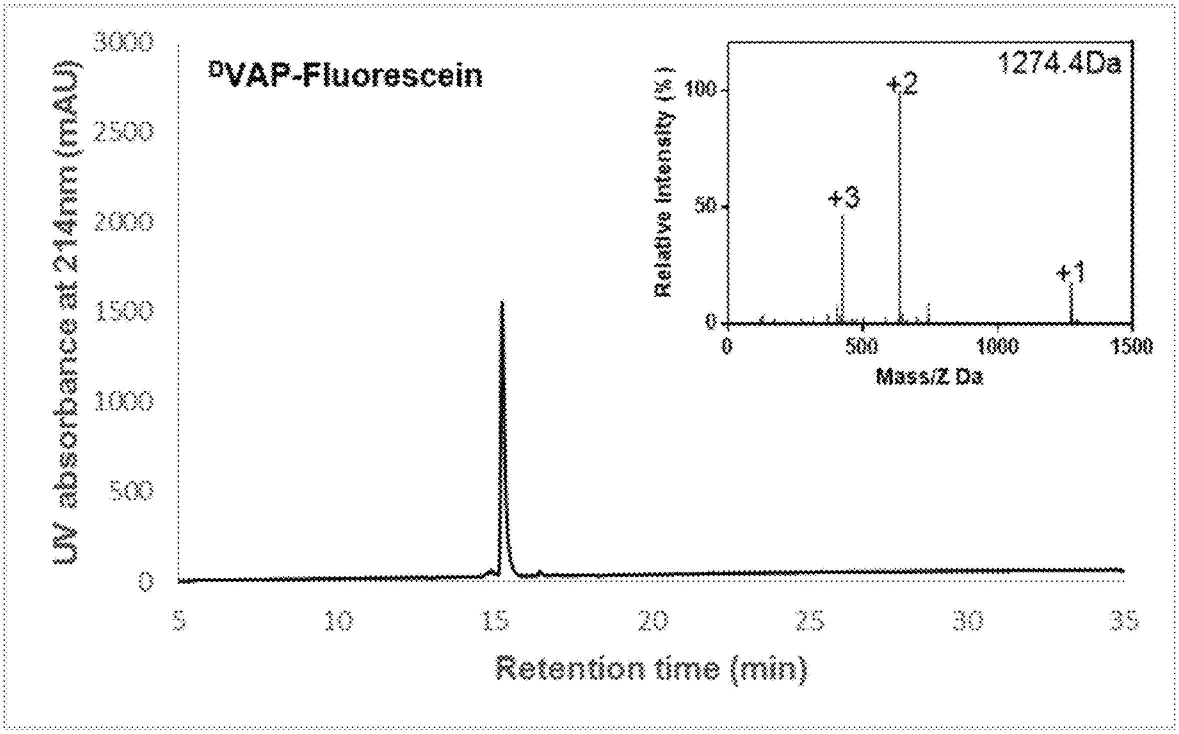
FIG. 7 shows the HPLC and ESI-MS spectra of $^{D}$VAP-Fluorescein: The chromatographic method was the same as above, and the retention time was 15.3 min. ESI-MS: 1274.4, in accordance with the theoretical molecular weight.
Figure 8:
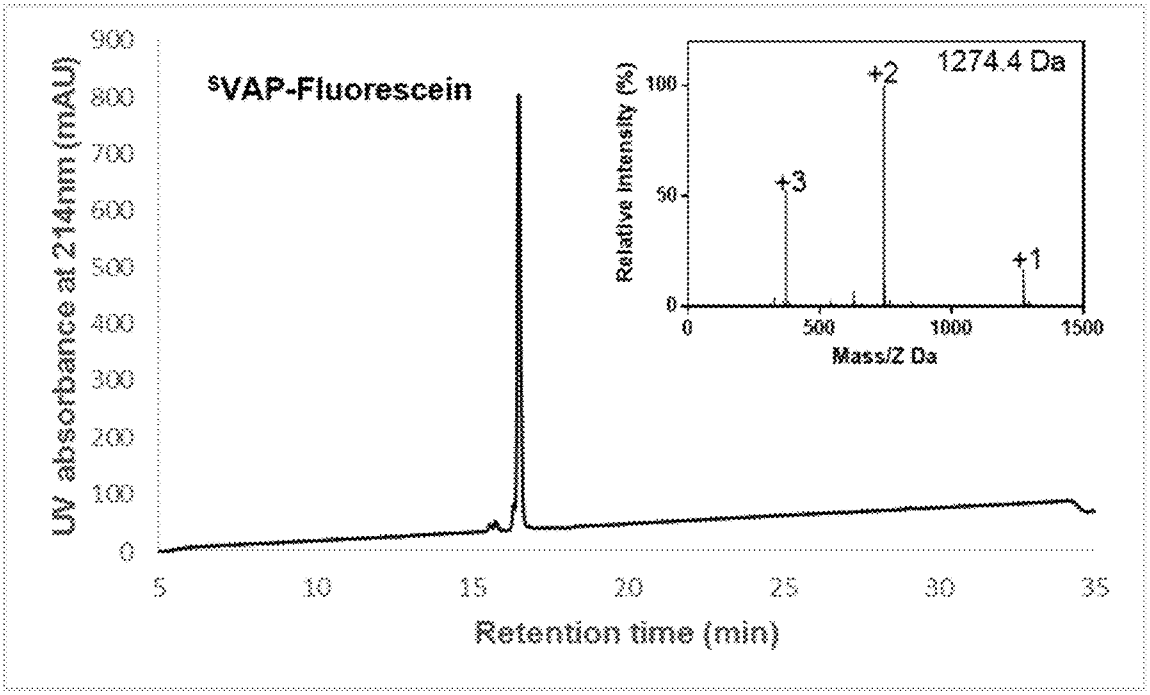
FIG. 8 shows the HPLC and ESI-MS spectra of $^{S}$VAP-Fluorescein: The chromatographic method was the same as above, and the retention time was 16.9 min. ESI-MS: 1274.4, in accordance with the theoretical molecular weight.
Figure 9:
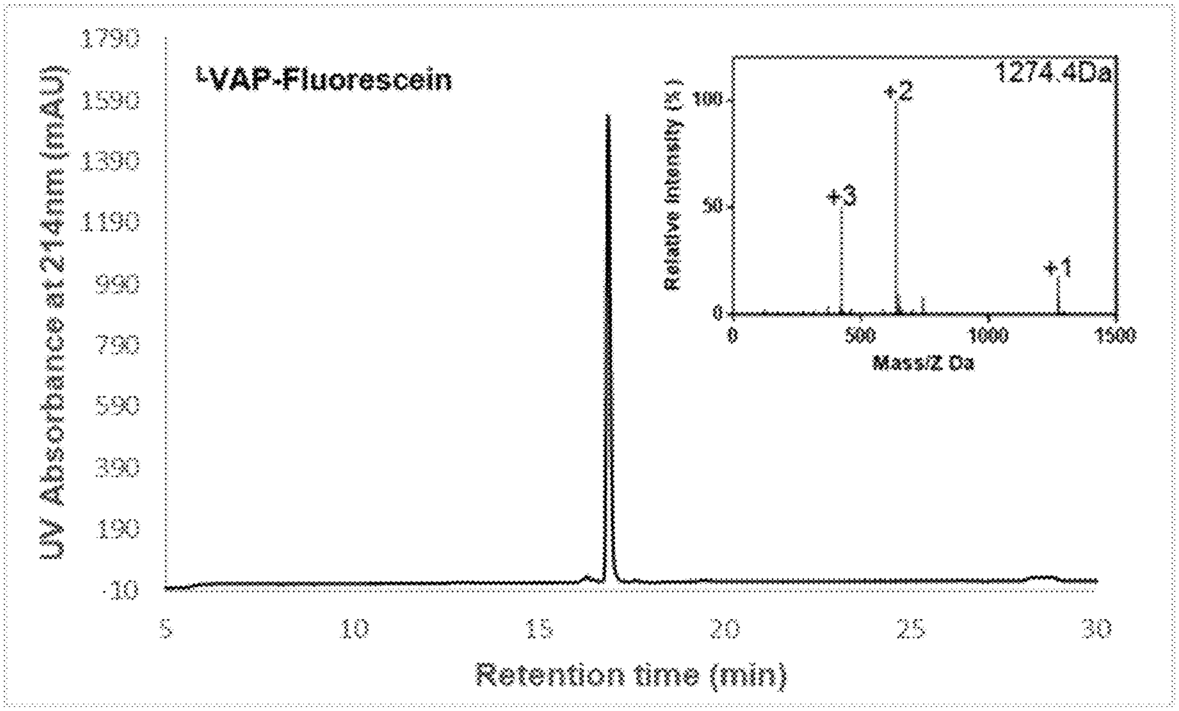
FIG. 9 shows the HPLC and ESI-MS spectra of $^{L}$VAP-Fluorescein: The chromatographic method was the same as above, and the retention time was 16.5 min. ESI-MS: 1274.4, in accordance with the theoretical molecular weight.

The $^{D}$VAP-Cys, $^{S}$VAP-Cys or $^{L}$VAP-Cys obtained in the above step were dissolved in 0.1 M PBS solution (pH 7.2), and Fluorescein-5-maleimide was dissolved in DMF. After mixing, the react solution was stirred magnetically, and monitored by HPLC. The reaction was stopped when the $^{D}$VAP-Cys, $^{S}$VAP-Cys or $^{L}$VAP-Cys completely reacted, and the react solution was purified by preparative HPLC with acetonitrile/water (containing 0.1% TFA) as eluent and freeze-dryed to obtain $^{D}$VAP-Fluorescein, $^{S}$VAP-Fluorescein or $^{L}$VAP-Fluorescein. HPLC spectra and mass spectra are shown in FIGS. 7, 8, and 9.

Figure 10:
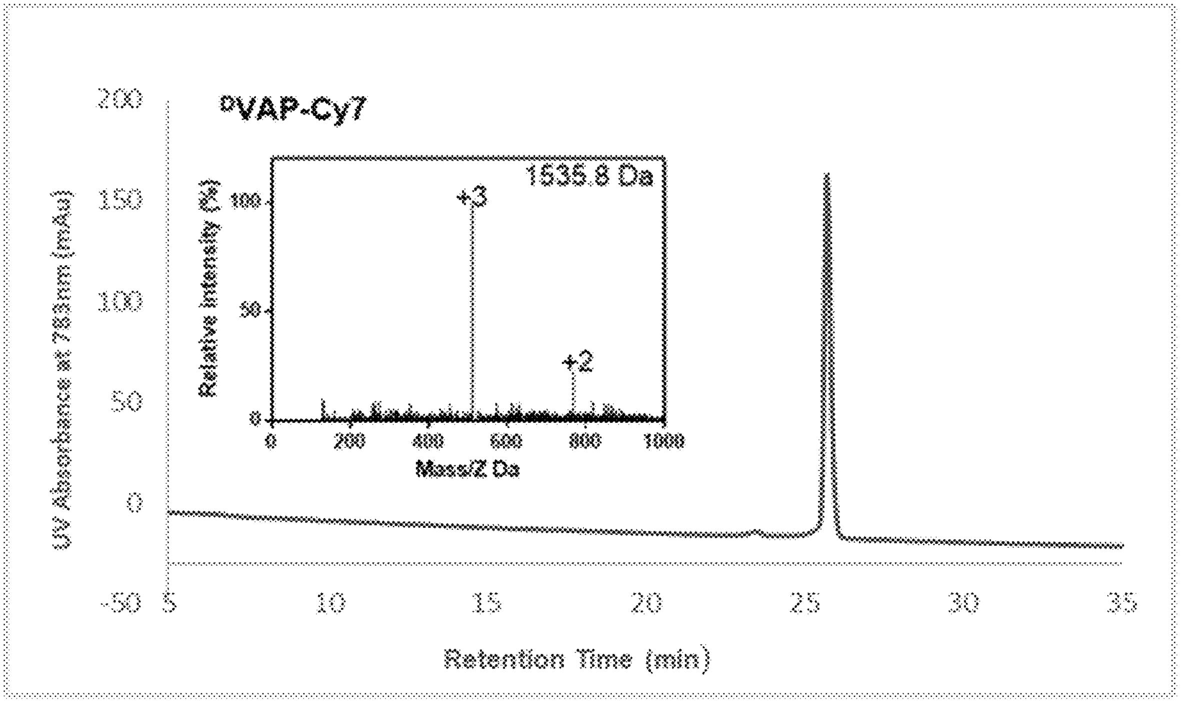
FIG. 10 shows the HPLC and ESI-MS spectra of $^{D}$VAP-Cy7: The chromatographic method was the same as above, and the retention time was 26.5 min. ESI-MS: 1535.8, in accordance with the theoretical molecular weight.
Figure 11:
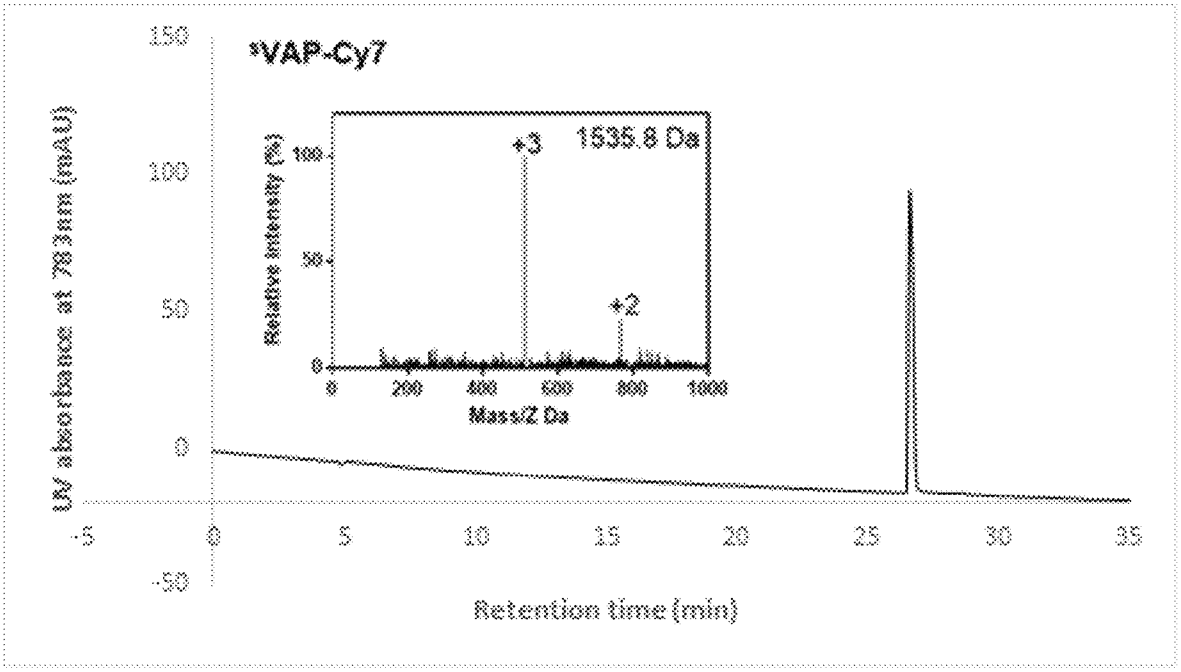
FIG. 11 shows the HPLC and ESI-MS spectra of $^{S}$VAP-Cy7: The chromatographic method was the same as above, and the retention time was 26.5 min. ESI-MS: 1535.8, in accordance with the theoretical molecular weight.
Figure 12:
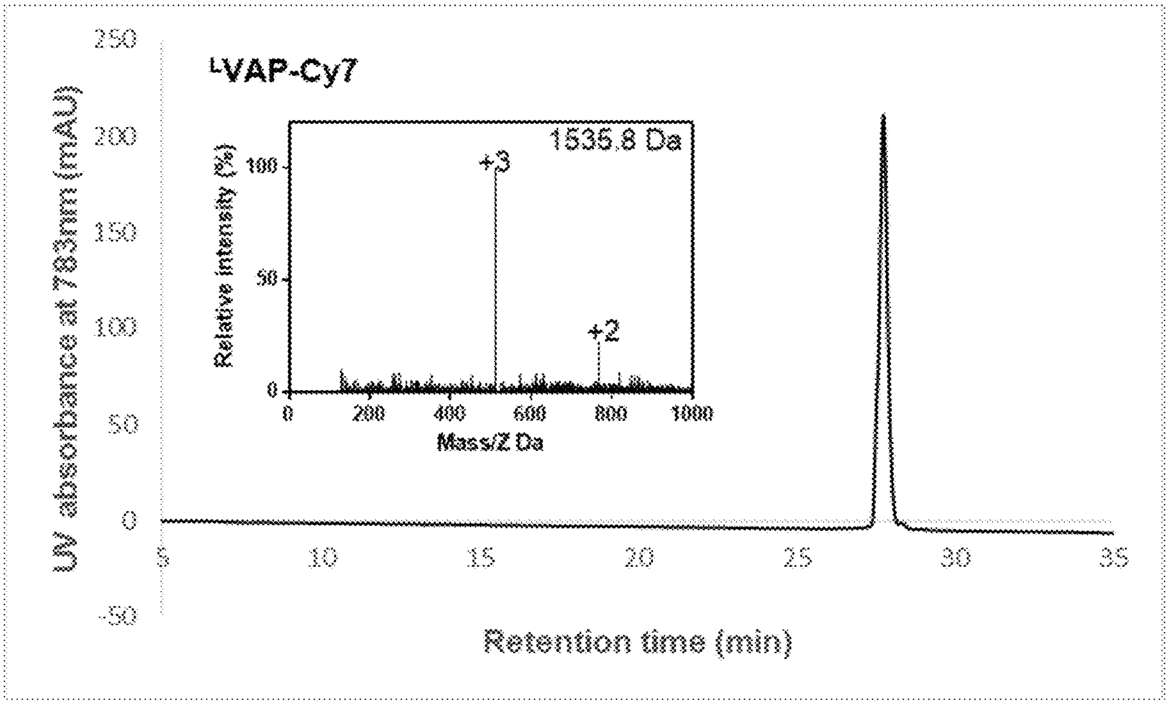
FIG. 12 shows the HPLC and ESI-MS spectra of $^{L}$VAP-Cy7: The chromatographic method was the same as above, and the retention time was 26.5 min. ESI-MS: 1535.8, in accordance with the theoretical molecular weight.

The preparation method of VAP-Cy7 was the same as above. HPLC spectra and mass spectra are shown in FIGS. 10, 11, and 12.

3. Preparation of VAP-DTPA-Gd and VAP-DTPA-$^{99m}$Tc

Maleimide-DTPA dissolved in DMF was mixed and stirred with $^{D}$VAP-Cys, $^{S}$VAP-Cys or $^{L}$VAP-Cys contained PBS solution for reaction as above. Prepare HPLC and freeze-drying were applied to obtain pure $^{D}$VAP-DTPA, $^{S}$VAP-DTPA or $^{L}$VAP-DTPA, followed by chelating with Gd or $^{99m}$Tc to obtain VAP-DTPA-Gd or VAP-DTPA-$^{99m}$Tc.

4. Preparation of VAP-Drug Complex

Figure 13:
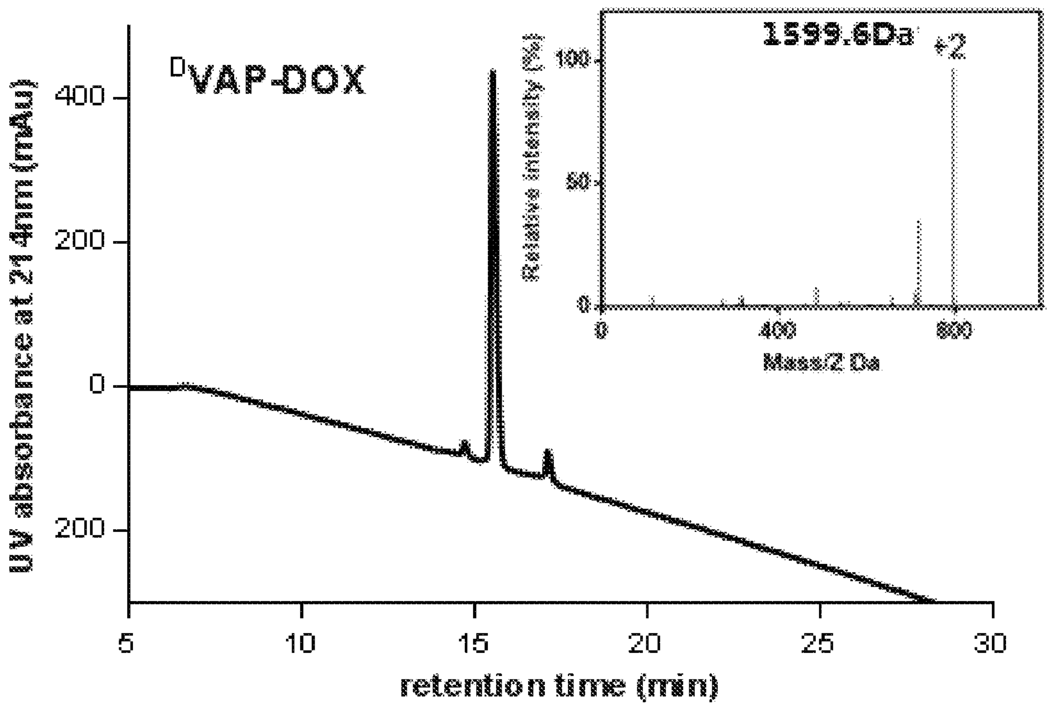
FIG. 13 shows the HPLC and ESI-MS spectra of $^{D}$VAP-DOX: The chromatographic method was the same as above except that 0.1% trifluoroacetic acid was replaced by 0.1% formic acid in the mobile phase, and the retention time was 15.5 min. ESI-MS: 1599.6, in accordance with the theoretical molecular weight.

VAP-doxorubicin complex was prepared as an example of VAP conjugated with drugs containing ketone or aldehyde group. 9.4 mg thiolated VAP ($^{D}$VAP or $^{S}$VAP or $^{L}$VAP) was dissolved in 3 mL PBS (0.1 mM, pH 7.0) and 10 times molar amount of tris(2-carboxyethyl) phosphine (TCEP) was added, and stirred at 4° C. for 20 min. Then, 4 times molar amount of doxorubicin maleimidohydrazine derivative (MAL-DOX) was added and reacted at room temperature in the dark for 1 h. The reaction solution was purified by preparative HPLC and lyophilized to obtain $^{L}$VAP or $^{D}$VAP or $^{S}$VAP-doxorubicin complex. The complexes were characterized by HPLC and MS. The results are shown in FIG. 13.

VAP-paclitaxel complex was prepared as an example of VAP conjugated with drugs containing hydroxyl or amino group by disulfide bond. 200 mg paclitaxel was dissolved in 10 mL chloroform, cooled to 0-5° C., and 39.99 mg DCC and 60.4 mg 3-(2-pyridyldithio) propionic acid were successively added, then the reaction solution was raise to room temperature to react overnight. The reaction solution was filtered and purified by column chromatography (CHCl3/MeOH=50:1-15:1, V/V elution) to obtain paclitaxel 3-(2-pyridinyl)-propionic acid derivative. Paclitaxel 3-(2-pyridinyl)-propionic acid derivative was dissolved in 5 mL DMF, and 1.5 times molar amount of VAP-Cys was dissolved in PBS/DMF. Paclitaxel 3-(2-pyridinyl)-propionic acid derivative was droply added to the thiol peptide solution, and the pH of the solution was maintained at 4-5 and reacted at room temperature for 6 h. The VAP-paclitaxel complex was obtained by preparative HPLC purification and lyophilizing.

VAP-bortezomib complex was prepared as an example of VAP conjugated with drugs containing boronic acid group. After the amino acids was sequentially coupled to the resin according to the synthesis of VAP and trifluoroacetic acid removed Boc protection at the nitrogen end, 3 times molar amount of succinic anhydride with DIEA dissolved in DMF was added and reacted at room temperature for 30 min. After washing the resin, 5 times molar amount of trimethylchlorosilane was added to react for 1 hour at room temperature for dopeamine protection, and HBTU/DIEA was used as condensing agent. The resin was cleavaged by hydrogen fluoride and VAP-dopamine derivative was purified by preparative HPLC. The VAP-dopamine derivative was mixed with bortezomib in buffer of pH 7.4 at a molar ratio of 1:1 to obtain the VAP-bortezomib complex.

VAP-PMI was prepared as an example of VAP conjugated with peptide drugs. The VAP-drug complex was obtained directly by solid phase peptide synthesis method. The specific method is: after the VAP-PMI polypeptide sequence disigned, the amino acids of VAP-PMI was sequentially coupled to resin by the same method as the preparation of VAP, and the VAP-PMI fusion peptide was obtained after hydrogen fluoride cleavage and purification.

5. Synthesis and Characterization of VAP-PEG-PLA

Figure 14:
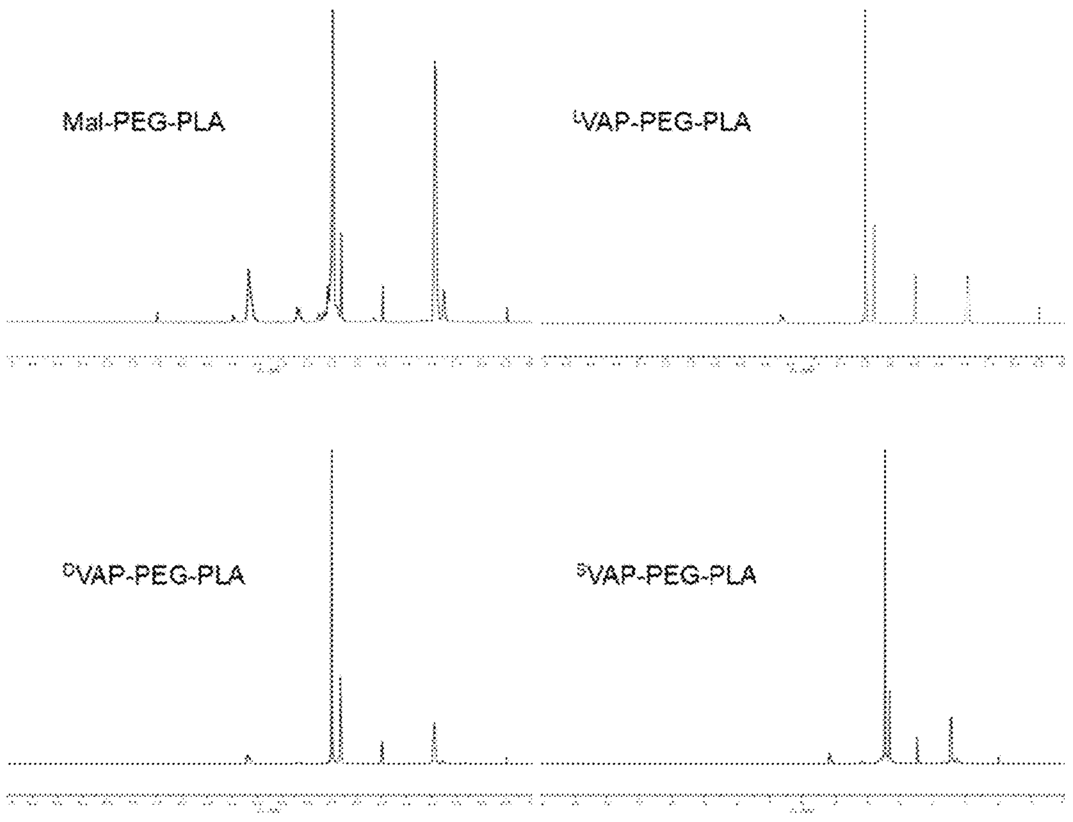
FIG. 14 shows $^{1}$H-NMR spectra of $^{D}$VAP-PEG$_{3000}$-PLA$_{2000}$, $^{S}$VAP-PEG$_{3000}$-PLA$_{2000}$ and $^{L}$VAP-PEG$_{3000}$-PLA$_{2000}$: The nuclear magnetic spectrum of Mal-PEG-PLA showed a maleimide peak at 6.7 ppm, while the peak disappeared in the nuclear magnetic spectrum of VAP-PEG-PLA, indicating that the maleimide group in Mal-PEG-PLA has reacted completely.

The synthesis of the polymer material was achieved by the reaction of free sulfhydryl group of the peptide with the maleimide group in Mal-PEG-PLA. 40 mg Mal-PEG-PLA was dissolved in 5 mL acetonitrile, rotary evaporated to form film, and 3 mL PBS (pH 8.0, 0.2 M) was added to hydrate to form micelles at 37° C., then 9.6 mg VAP-Cys was added within 8 hours for reacting overnight. Excess VAP-Cys was removed by dialysis, and the reaction was detected by HPLC. VAP-PEG-PLA was lyophilized and characterized by $^{1}$H-NMR (FIG. 14).

EXAMPLE 2

Figure 15:
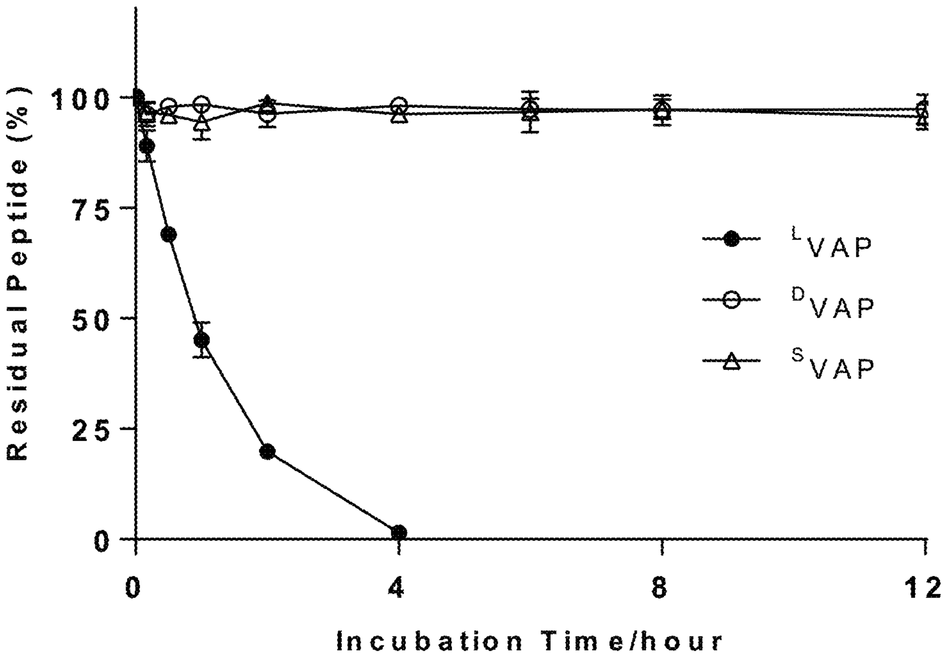
FIG. 15 shows serum stability of $^{D}$VAP, $^{S}$VAP and $^{L}$VAP: The vertical ordinate of the graph is the residual percentage of intact polypeptide. It can be seen that the stability of $^{D}$VAP and $^{S}$VAP in 50% mouse serum is significantly higher than that of $^{L}$VAP. After 2 h incubation, $^{L}$VAP completely degraded, while $^{D}$VAP and $^{S}$VAP hardly degraded.

Investigation of Serum Stability of VAP $^{D}$VAP, $^{S}$VAP and $^{L}$VAP were dissolved in distilled water at 1 mg/mL respectively, then 0.1 mL of each VAP solution was added to 0.9 mL 25% mouse serum and incubated at 37° C. At 0 and 15 min, 0.5, 1, 2 and 4 h, 100 μL solution was taken out and 20 μL trichloroacetic acid (TCA) was added to precipitate protein of the serum, after standing for 20 min at 4° C., the solution was centrifuged at 12,000 rpm for 10 min. 20 μL supernatant was taken for HPLC analysis. Serum stability results (FIG. 15) indicate that $^{D}$VAP and $^{S}$VAP have better serum stability than $^{L}$VAP.

EXAMPLE 3

Experiment of Binding Activity of VAP to Glucose-Regulated Protein GRP78

Pre-binding analysis was performed by the biacore system, and pH 5.0 was selected as the optimal pH for GRP78 binding to the CMS chip. Recombinant human GRP78 was coupled to the CM5 chip and the RU value reached the predetermined value. $^{D}$VAP, $^{S}$VAP, and $^{L}$VAP solution were prepared at concentrations of 0.3125, 0.625, 1.25, 2.5, 5, 10, and 20 μM, respectively. The samples were injected from low to high concentration. The binding activities of $^{D}$VAP, $^{S}$VAP and $^{L}$VAP to protein were analyzed by Biacore T200

Figure 16:
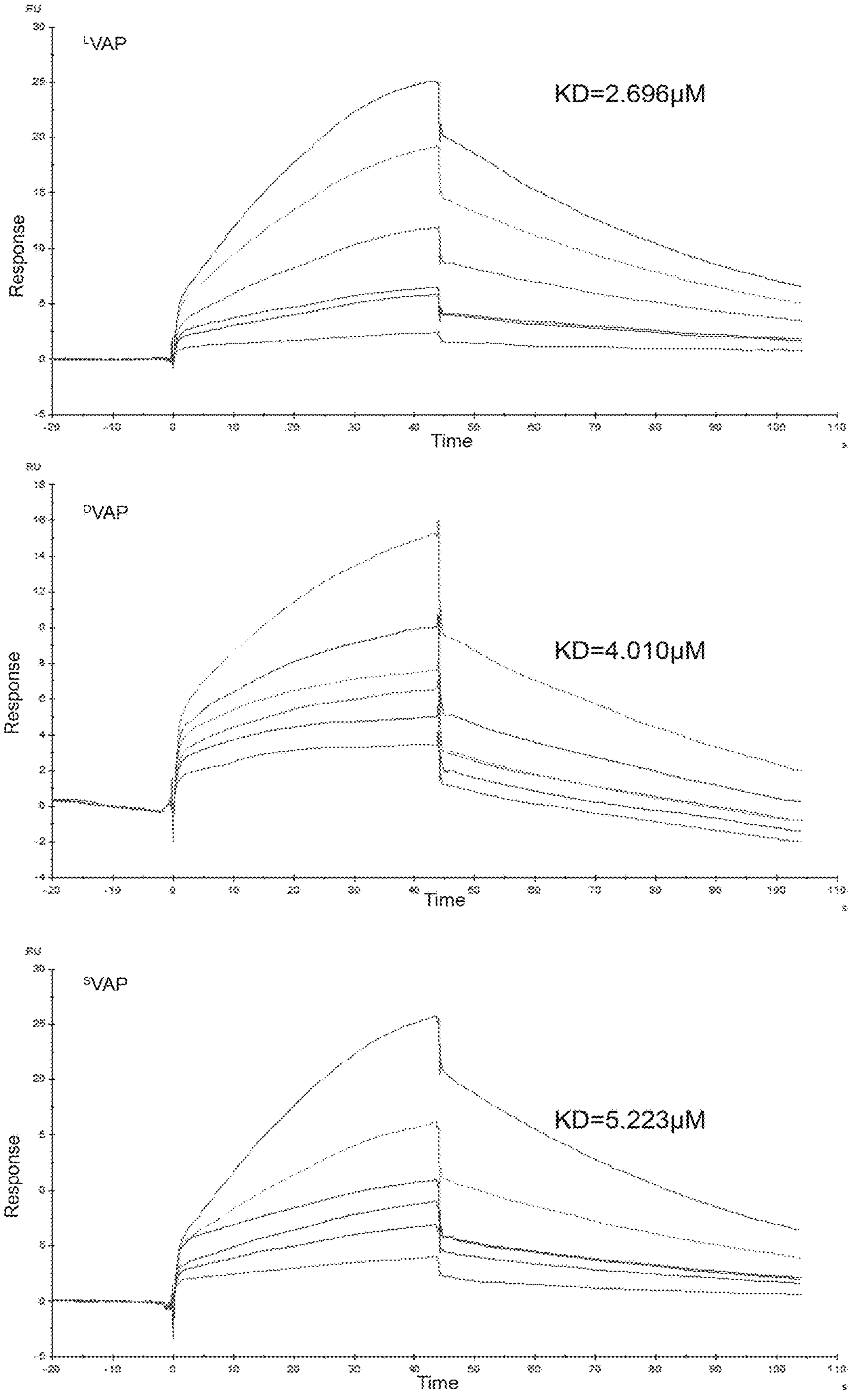
FIG. 16 shows the binding capacity of $^{D}$VAP, $^{S}$VAP and $^{L}$VAP to GRP78: $^{D}$VAP, $^{S}$VAP and $^{L}$VAP have similar binding capacities to GRP78 with KD values of 4.010 μM and 5.223 μM, 2.696 μM, respectively, which $^{D}$VAP and $^{S}$VAP are slightly weaker than $^{L}$VAP. The dissociation patterns of the three peptides are similar, with Kd values of 0.02091 1/s, 0.02826 1/s, and 0.01898 1/s, respectively.

Evaluation software, and the $K_D$ value and Kd value were calculated respectively (FIG. 16).

EXAMPLE 4

Investigation of Intracellular Distribution of GRP78

Figures 17A, 17B, 17C:
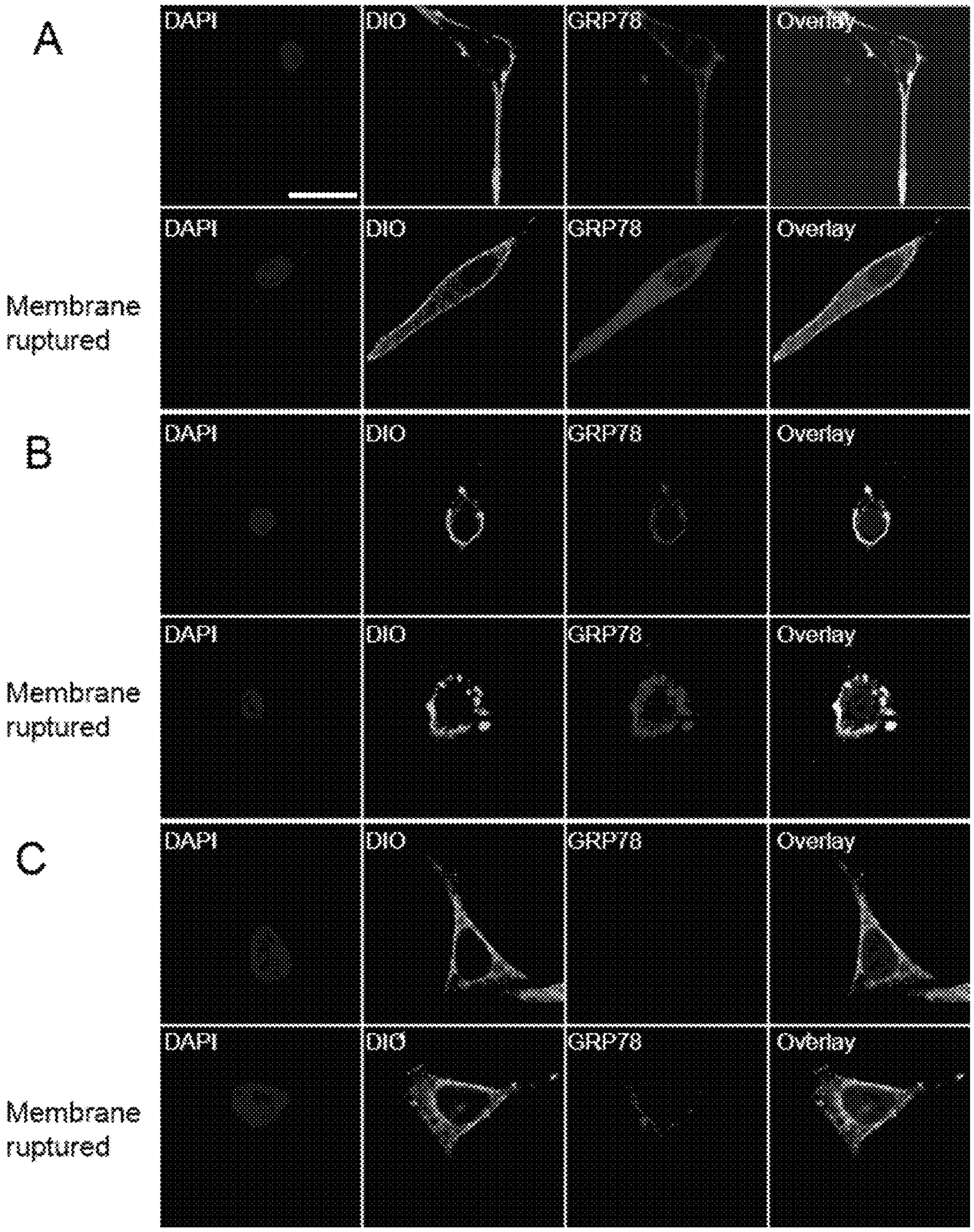
FIG. 17 shows the intracellular distribution of GRP78: GRP78 has wide distribution on the cell membrane and in plasm of tumor cell U87 and HUVEC (Human Umbilical Vein Endothelial Cells), while no distribution on the membrane and small distribution in plasm of HEK293 (normal cell).

Three kinds of cells (U87, HUVEC and HEK293) were chosen for GRP78 distribution experiment, and the distribution of GRP78 in cells was investigated with membrane rupture and no membrane rupture. The cells were inoculated into confocal dishes, washed three times with PBS, and fixed with 10 μM DIO paraformaldehyde solution for 8 min. After blocked with 1% BSA at 37° C. for 30 min and washed three times with PBS, the cells were added with anti-GRP78 antibody diluted by 1% BSA and incubated at 37° C. for 4 h. Then the cells were washed twice with PBS and added with secondary antibody diluted by 1% BSA, incubated at 37° C. for 2 h and washed twice with PBS for 5 min each time. After stained with DAPI for 10 min and washed three times with PBS and glycerin-sealed, the cells were observed with laser confocal. The results are shown in FIG. 17.

EXAMPLE 5

In Vitro Cell Targeting of VAP Assay

1. In Vitro Targeting of VAP to Glioma Cell U87

Monolayer cultured glioma cell (U87 cell) in logarithmic growth phase were digested with 0.25% trypsin. Use DMEM culture solution containing 10% fetal bovine serum to prepare single cell suspension. The culture plate was transferred to a carbon dioxide incubator and the cells were cultured into 12-well plates at a density of $1\times10^5$ cells per well with the well volume of 1 mL overnight at 37° C., 5% $CO_2$ and saturated humidity. Then the DMEM medium was replaced with FAM, $^D$VAP-Fluorescein, $^S$VAP-Fluorescein and $^L$VAP-Fluorescein solution at concentration of 5 μM prepared with DMEM culture solution containing 10% fetal bovine serum and incubated at 37° C. for 4 h and the supernatant was aspirated. The cells were washed three times with PBS solution, fixed with formaldehyde, and stained with DAPI. The fluorescence images were captured by a confocal laser microscope. The photos of cell internalization are shown in FIG. 18A. The cells were washed three times by PBS, and then detected by flow cytometry. The result of flow cytometry analysis is shown in FIG. 18B.

2. In Vitro Targeting of VAP to Human Umbilical Vein Endothelial Cells

Monolayer cultured human umbilical vein endothelial cells (HUVEC cells) in logarithmic growth phase were tested as above, and the internalization photo is shown in FIG. 19A and the result of flow cytometry analysis is shown in FIG. 19B.

Figures 20A, 20B:
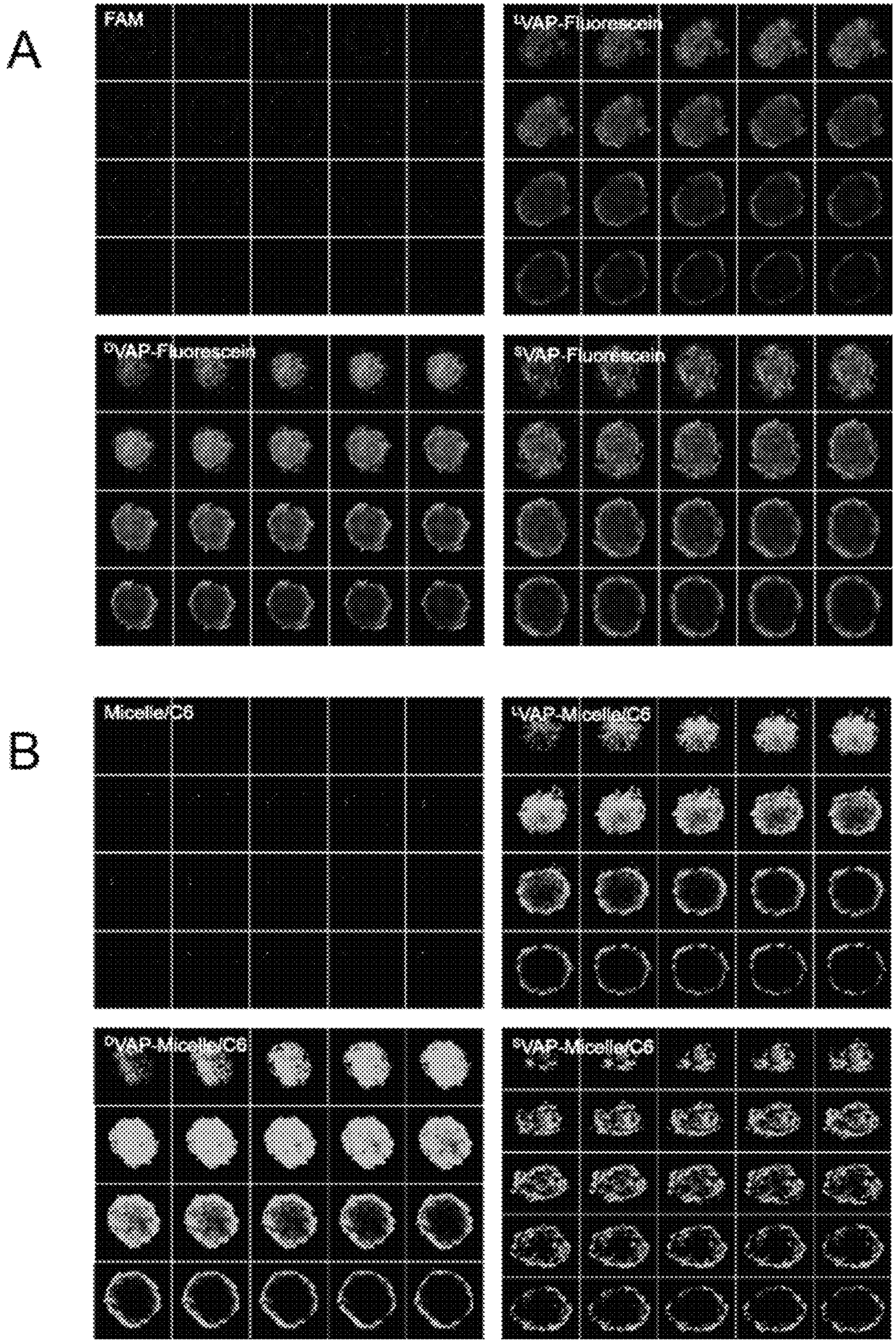
FIGS. 20A-20B show the uptake of Fluorescein-labeled peptide and VAP-Micelle/C6 by U87 tumor spheroids: The figures show the uptake of each of the Fluorescein-labeled peptides and VAP micelles by U87 tumor spheroids. It can be seen from the figures that each of the fluorescein-labeled peptides and VAP micelles can be well taken up by U87 tumor spheroids, which is significantly different from the FAM and plain micelles.

3. Targeting of VAP to U87 Tumor Spheroids In Vitro 2% low molecular weight agarose solution was added to a 48-well plate while it is hot, 150 μL per well, and placed at room temperature for cooling and solidification. Then, 400 μL U87 cell suspension was inoculated per well, and the cell density was $2\times10^3$ cells/well. The tumor spheroids were established by incubating in carbon dioxide incubator for 7 days at 37° C., 5% $CO_2$ and saturated humidity. Then the culture solution was replaced with FITC, $^D$VAP-Fluorescein, $^S$VAP-Fluorescein and $^L$VAP-Fluorescein solution at concentration of 5 μM prepared with DMEM culture solution containing 10% fetal bovine serum for 4 h at 37° C. and the supernatant was aspirated. The tumor spheroids were washed three times with PBS, fixed with paraformaldehyde for 15 minutes, then observed by confocal microscope. The photograph is shown in FIG. 20A.

Figure 21:
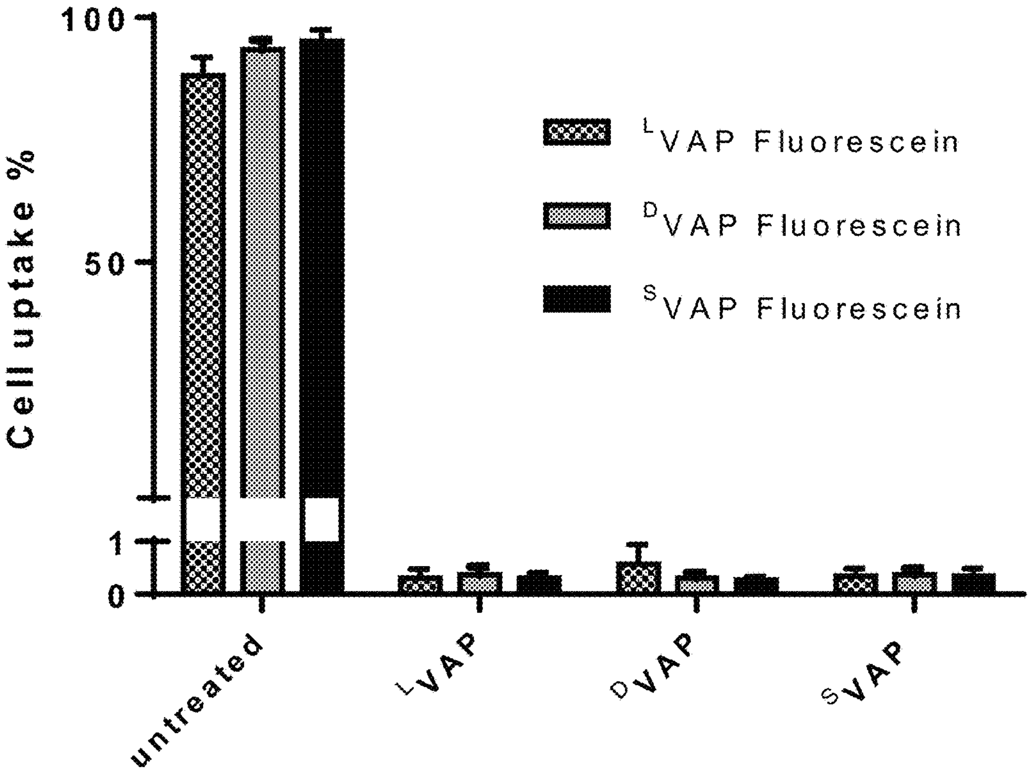
FIG. 21 shows the competitive inhibition of $^{D}$VAP, $^{S}$VAP and $^{L}$VAP: It can be seen that $^{D}$VAP, $^{S}$VAP and $^{L}$VAP can completely inhibit each other, and it is proved that all three polypeptides bind to the same site of GRP78 protein.

4. VAP Mutual Competition Inhibition Test 9 groups (blank control group, $^L$VAP-Fluorescein, $^D$VAP-Fluorescein, $^S$VAP-Fluorescein, $^L$VAP-Fluorescein(+$^L$VAP), $^L$VAP-Fluorescein(+$^D$VAP), $^L$VAP-Fluorescein(+$^S$VAP), $^D$VAP-Fluorescein(+$^L$VAP), $^D$VAP-Fluorescein(+$^D$VAP), $^D$VAP-Fluorescein(+$^S$VAP), $^S$VAP-Fluorescein(+$^L$VAP), $^S$VAP-Fluorescein(+$^D$VAP), $^S$VAP-Fluorescein(+$^S$VAP)) were set with 3 tubes each group to investigate the mutual competition inhibition between VAP peptides. U87 cells were digested by trypsin and transferred to EP tubes, washed with PBS three times to remove trypsin, pretreated at 4° C. for 20 min. The prepared peptide solution (non-fluorescent label) was also placed at 4° C. for low temperature pretreatment, then the peptide solution was mixed with the cells and shocked for 2 h to saturate the receptor protein on the cell surface. Then the fluorescein-labeled peptide solution was added. After standing overnight at 4° C., the cells were washed 3 times with PBS, and analyzed by flow cytometry (as shown in FIG. 21).

EXAMPLE 6

In Vivo Tumor Targeting of VAP Assay

Figures 22A, 22B, 22C, 22D:
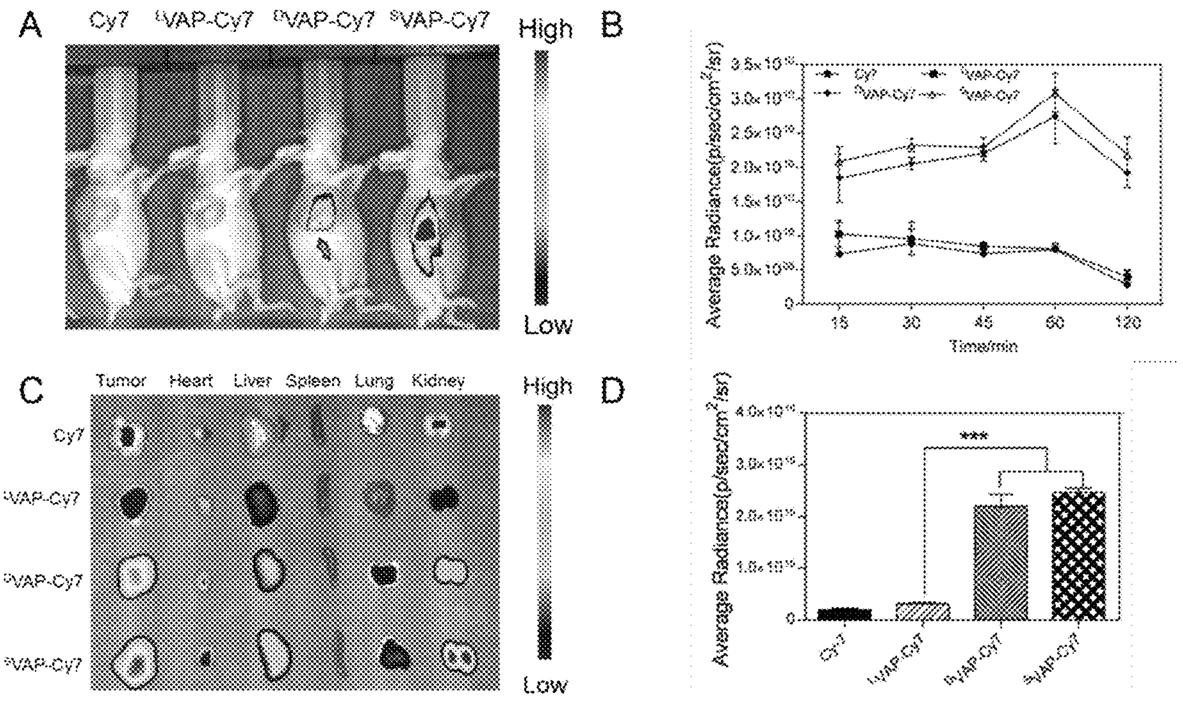
FIGS. 22A-22D show the distribution of Cy7-labeled peptides in subcutaneous transplant tumor.

Firstly, a subcutaneous tumor animal model was constructed as follows: U87 cells in the logarithmic growth phase were digested with trypsin, then 100 μL cell suspension at concentration of $3\times10^7$/mL was inoculated to the right dorsum of the nude mice. The mice were raised in the SPF class and the tumor size was observed regularly. When the tumor size was 200 $mm^3$, the tumor-bearing nude mice without necrosis and with regular tumor shape were selected and tested in groups. Cy7 and $^D$VAP-Cy7, $^S$VAP-Cy7 and $^L$VAP-Cy7 solutions were injected into the tumor-bearing nude mice model through the tail vein at the dose of 0.15 μmol per mouse. After 2 hours, the nude mice were sacrificed, and the tumor was harvested and exposed to ex vivo fluorescence imaging by IVIS imagine systems (as shown in FIG. 22A). Besides, the semi-quantitative analysis of fluorescence intensity was calculated (as shown in FIG. 22B). FIG. 22C shows the ex vivo fluorescence images in tumors and organs. FIG. 22D is the ex vivo semi-quantitative analysis of fluorescence intensity in tumor. The accumulation of Cy7-labeled $^D$VAP, $^S$VAP and $^L$VAP in tumors was significantly higher than that of free Cy7 (***$p<0.001$), and the tumor targeting effect is: $^D$VAP≈$^S$VAP>$^L$VAP.

EXAMPLE 7

Pharmacodynamics and Pharmacokinetic Validation of $^D$VAP-DOX

1. Inhibition Efficacy Test of U87 Subcutaneous Tumor

The U87 subcutaneous tumor-bearing mice model was constructed and tested in groups when the tumor size was 100 $mm^3$. The subcutaneous tumor-bearing model mice were administrated with saline, DOX, MAL-DOX (at high and low dose) and $^D$VAP-DOX (at high and low dose) and RGD-DOX (drug complexes prepared by the same method according to VAP-DOX with integrin ligand c(RGDyK) and MAL-DOX) for five times and the interval between each dose was 2 days. The total dose of DOX was 2.5 mg/kg except 1.25 mg/kg for low dose. The long diameter (a) and short diameter (b) of the tumor were measured by vernier calipers every other day, and the tumor volume of nude mice was calculated according to the formula and the curve of tumor volume change with time was plotted, and the statistical difference of each group was calculated. The tumor volume was calculated according to the formula:

$$V_{tumor\ volume}=0.5\ (a\times b^2)$$

Figures 23A, 23B, 23C:
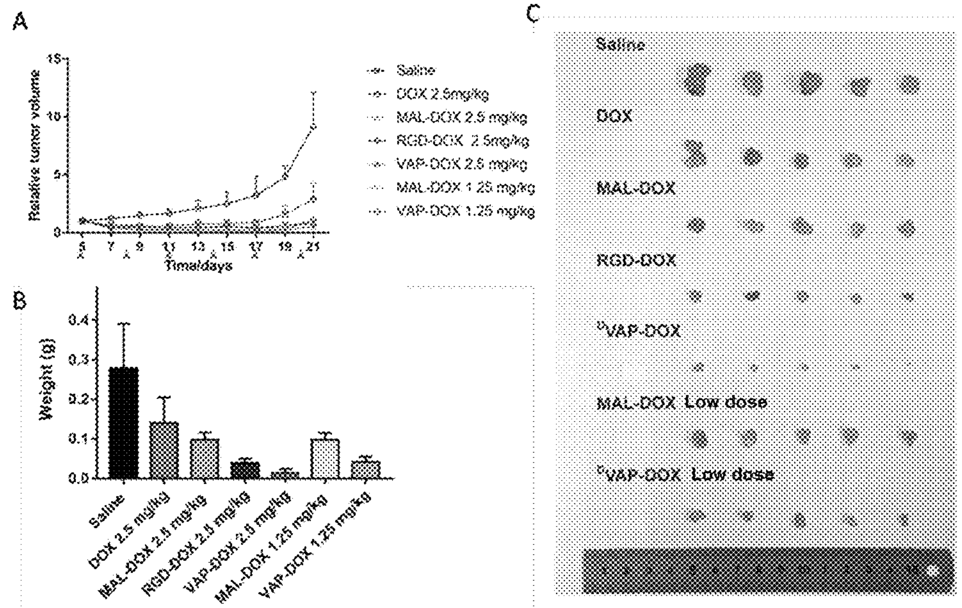
FIGS. 23A-23C show the subcutaneous tumor growth inhibition of $^{D}$VAP-DOX.

Twenty-one days after the administration, all nude mice were sacrificed, the harvested subcutaneous tumors were weighed, and the statistical difference and tumor inhibition rate of each group were calculated (FIGS. 23A-23C).

2. Anti-Glioblastoma Efficacy Test of Intracranial Glioma

Figure 24:
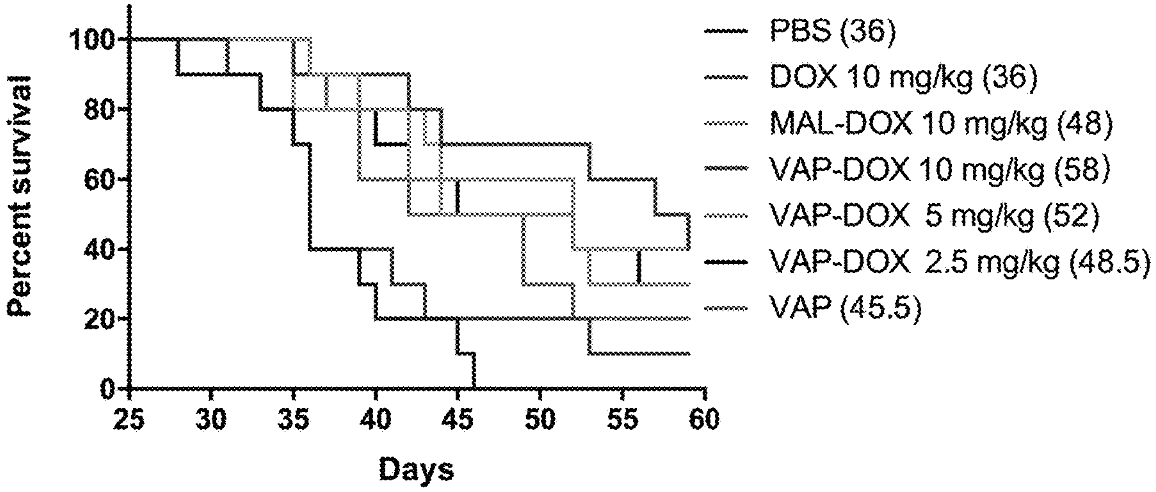
FIG. 24 shows the survival curves of nude mice model bearing intracranial tumor treated by $^{D}$VAP-DOX: The mean survival times of PBS group, DOX group, MAL-DOX group, $^{D}$VAP-DOX group (at high, medium, low dose) and the $^{D}$VAP group were 36, 36, 48, 58, 52, 48.5, and 45.5 days, respectively. The results showed that compared with the other groups, the survival time of nude mice model bearing intracranial tumor of $^{D}$VAP-DOX group prolonged the most, and the $^{D}$VAP-DOX at low dose had same anti-cerebral glioma effect of MAL-DOX at 4 times higher dose.

After the nude mice was anesthetized and fixed with stereotaxic apparatus, intracranial U87 tumor bearing model was established on nude mice by implanted with U87 cells ($5\times10^5$ cells dispersed in 5 μL of PBS buffer for each mouse) in the logarithmic growth phase into the right striatum (0.6 mm in front of the anterior iliac crest, 1.8 mm in the lateral direction, and 3 mm in depth). The status of naked mice was observed regularly. The mice were tail intravenously administrated with PBS, DOX, MAL-DOX, $^D$VAP, $^D$VAP-DOX (at high, medium and low dose) respectively at 10, 13, 16, 19 and 22 days post implantation. The total dose of DOX was 10 mg/Kg except 2.5 mg/Kg for low dose and 5 mg/kg for medium dose. The $^D$VAP dose was the amount of $^D$VAP contained in the high dose of $^D$VAP-DOX. The survival time of mice were recorded (FIG. 24).

3. Pharmacokinetic Study of $^D$VAP-DOX

Figure 25A:
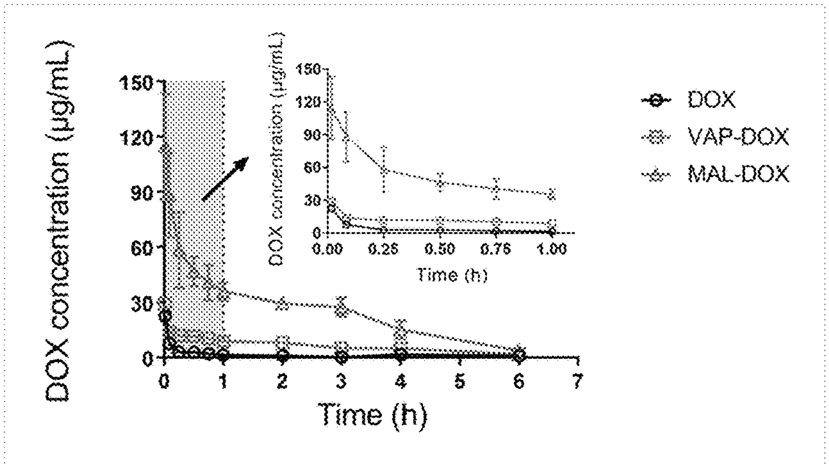
FIGS. 25A and 25B show the pharmacokinetic curve and distribution of $^{D}$VAP-DOX in mice.
Figure 25B:
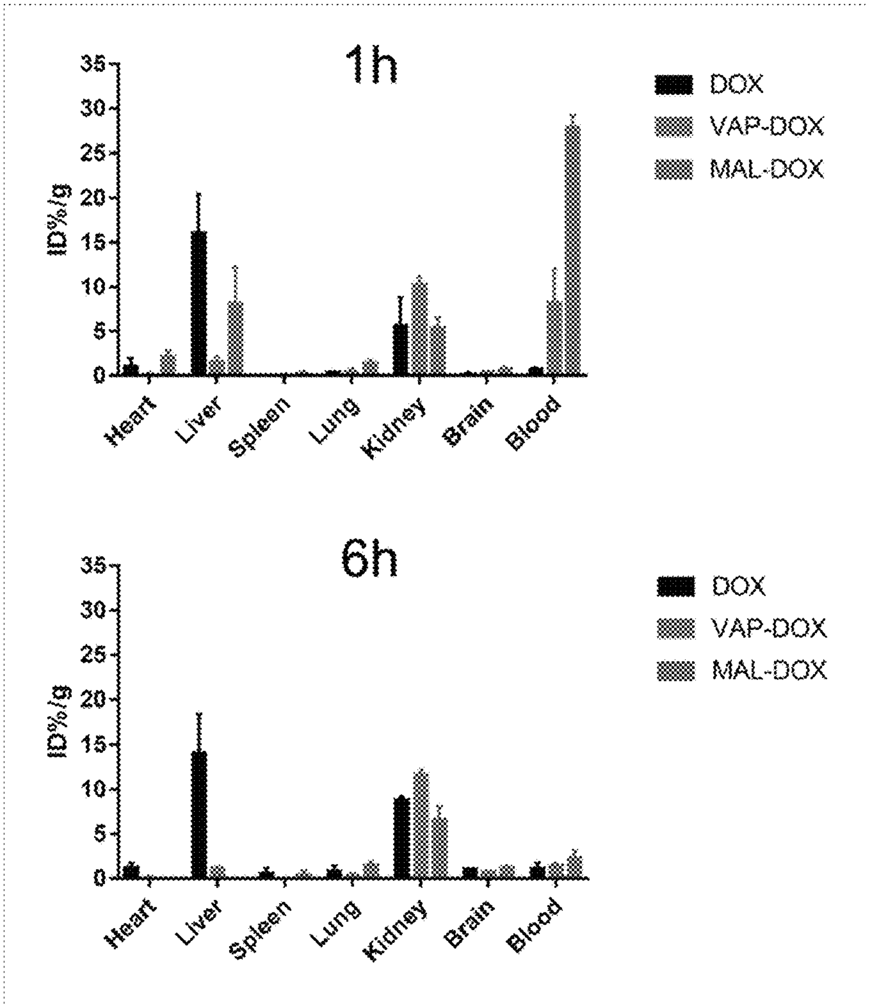

ICR mice were injected with 200 μL DOX, $^D$VAP-DOX and MAL-DOX (containing DOX of 10 mg/kg) through the tail vein respectively. At 1, 5, 15, 30 and 45 min, 1, 2, 4 and 6 h, 50 μL blood sample was collected and diluted 4 folds with PBS, which was measured by fluorescent Ex 485/Em 590 and the drug concentration-time curve and the distribution amount in main tissues were plotted (FIGS. 25A-25B).

EXAMPLE 8

Evaluation of In Vitro Tumor Spheroids Targeting Ability of Micelles

1. Preparation of Coumarin 6 Loaded Micelles 1 mg VAP-PEG-PLA, 9 mg mPEG-PLA and 5 ug coumarin 6 (C6) dissolved in 2 mL acetonitrile, evaporated decompressedly (~0.085 MPa) at 37° C. in water bath, to form thin film, which was hydrated with 2 mL physiological saline, and free coumarin was removed by CL-4B column chromatography to obtain coumarin 6-bated micelle (VAP-Micelle/C6).

2. In Vitro U87 Tumor Spheroids Targeting of VAP-Micelle/C6 Micelles Assay

2% low molecular weight agarose solution was added to a 48-well plate while it was hot with 150 μL per well, and U87 cells were seeded on 48-well plates at a density of $2\times10^3$/400 μL per well. Tumor spheroids were formed after incubating in carbon dioxide incubator for 7 days at 37° C., 5% $CO_2$ and saturated humidity. Then the culture solution was replaced with Micelle/C6, $^D$VAP Micelle/C6, $^S$VAP Micelle/C6 and $^L$VAP Micelle/C6 at concentration of 5 ng/mL prepared with DMEM culture solution containing 10% FBS. After 4 h incubation at 37° C., the supernatant was aspirated and the tumor spheroids were washed three times with PBS, fixed with paraformaldehyde for 15 minutes, then imaged using confocal microscope. The photograph is shown in FIG. 20B.

EXAMPLE 9

In vivo Targeting Verification of VAP Micelles

1. Preparation of DiR Loaded Micelles 1 mg VAP-PEG-PLA, 9 mg mPEG-PLA and 1 mg DiR was weighed and DiR loaded micelle (VAP-Micelle/DiR) was prepared according to the method of coumarin 6 loaded micelle.

2. In Vivo Targeting Validation of VAP-Micelle/DiR

Figures 26A, 26B:
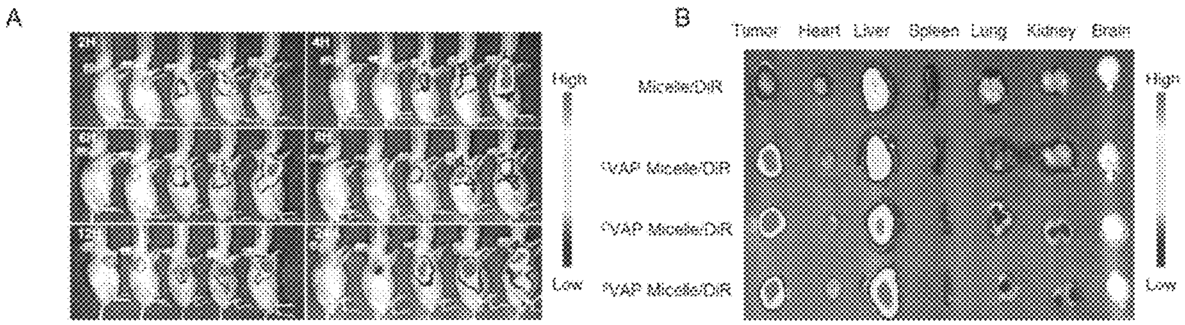
FIGS. 26A and 26B show the distribution of DiR loaded VAP micelles in subcutaneous tumor.

U87 subcutaneous tumor-bearing model nude mice were injected with 100 μL of PBS, mPEG-Micelle/DiR, $^D$VAP-Micelle/DiR, $^S$VAP-Micelle/DiR and $^L$VAP-Micelle/DiR respectively through the tail vein. The nude mice were anesthetized at 2, 4, 8, 12 and 24 h, and the distribution of DiR fluorescence in nude mice was recorded by IVIS imaging systems and semi-quantitative calculation of fluorescence intensity was performed (as shown in FIGS. 26A-26B).

EXAMPLE 10

Figure 27:
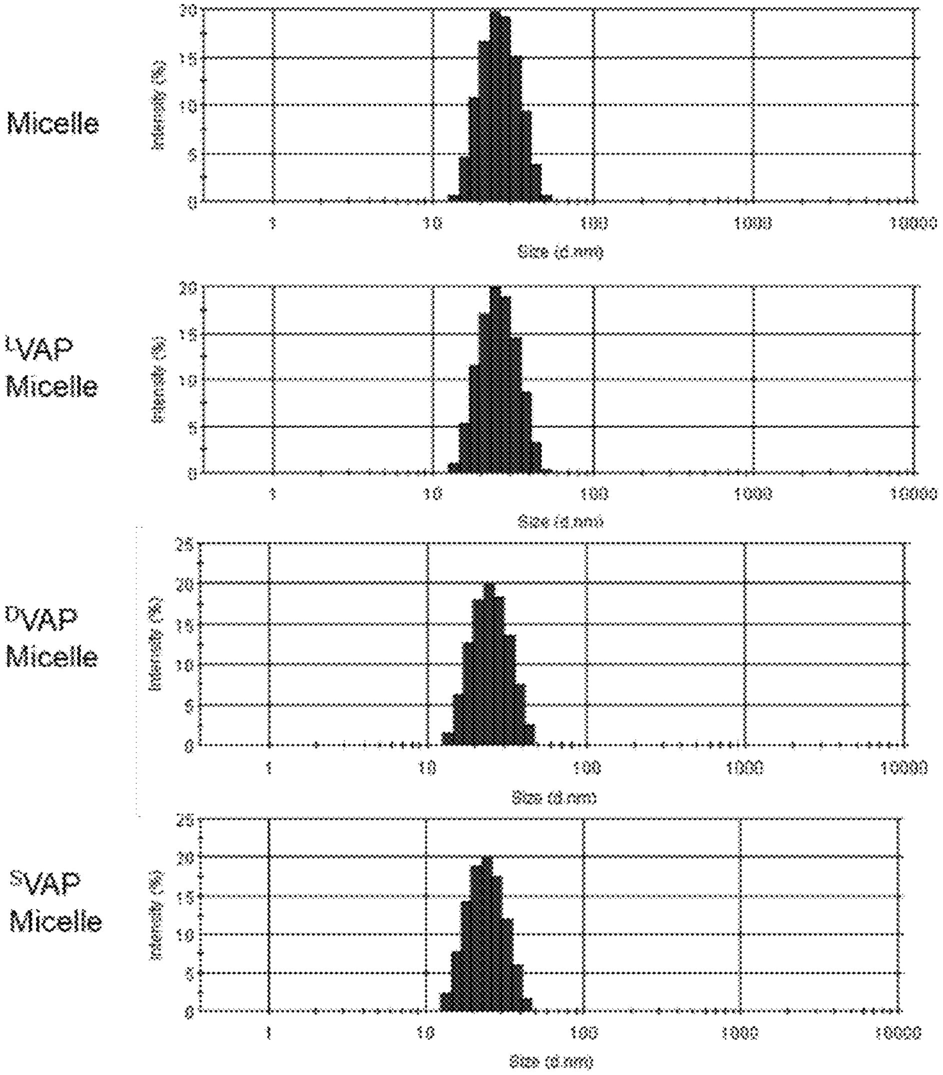
FIG. 27 shows the particle size of the paclitaxel loaded micelles: The figure shows the particle size distribution of each paclitaxel micelle formulation. As shown in the figure, there is no significant difference of size between different formulations.

In vitro Assessment of Anti-Glioma Efficacy of Paclitaxel Loaded VAP Micelles Preparation and Characterization of Paclitaxel Loaded Micelles 1 mg of VAP-PEG-PLA, 9 mg of mPEG-PLA and 2 mg of paclitaxel was weighed and paclitaxel loaded VAP micelles (VAP-Micelle/PTX) were prepared according to the method of coumarin 6 loaded micelles. The particle size and distribution are shown in FIG. 27.

2. In Vitro Assessment of Anti-Glioma Efficacy

Figures 28A, 28B:
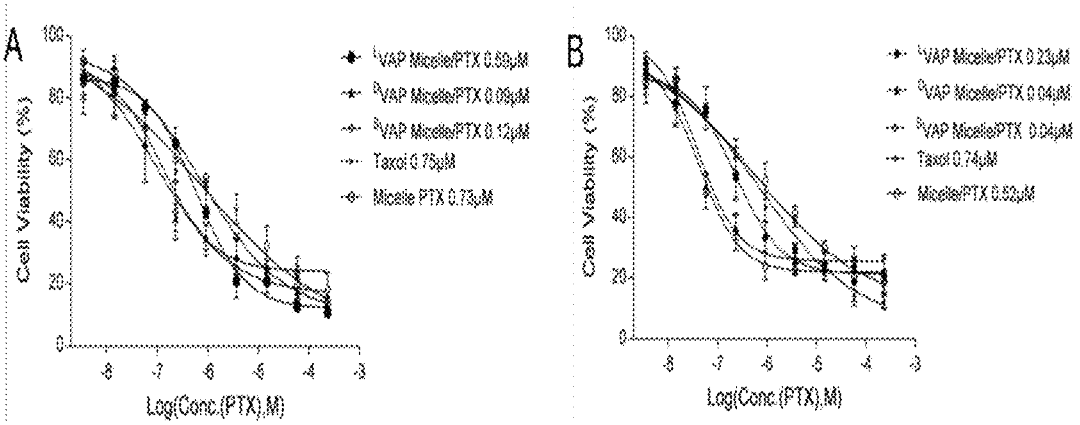
FIGS. 28A and 28B show inhibition curves of paclitaxel loaded micelles against U87 and HUVEC cells.

U87 cells were inoculated in 96-well plates with $4.0\times10^3$ cells/well. After 24 hours, the culture solution was replaced with 200 μL of a series of concentrations of $^D$VAP-Micelle/PTX, $^S$VAP-Micelle/PTX, $^L$VAP-Micelle/PTX and mPEG-Micelle/PTX and Taxol. 72 h later, 20 μL MTT solution was added to each well and incubated for another 4 h. Discarded the culture solution and added 150 μL DMSO and shaked the solution until the purple particles dissolved. Absorbance values were measured by microplate reader at 590 nm, and cell viability was determined by MTT assay, and cell viability and median lethal dose were calculated (as shown in FIGS. 28A-28B).

3. Inhibition Assay of VAP-Micelle/PTX on Neovascularization

Figure 29:
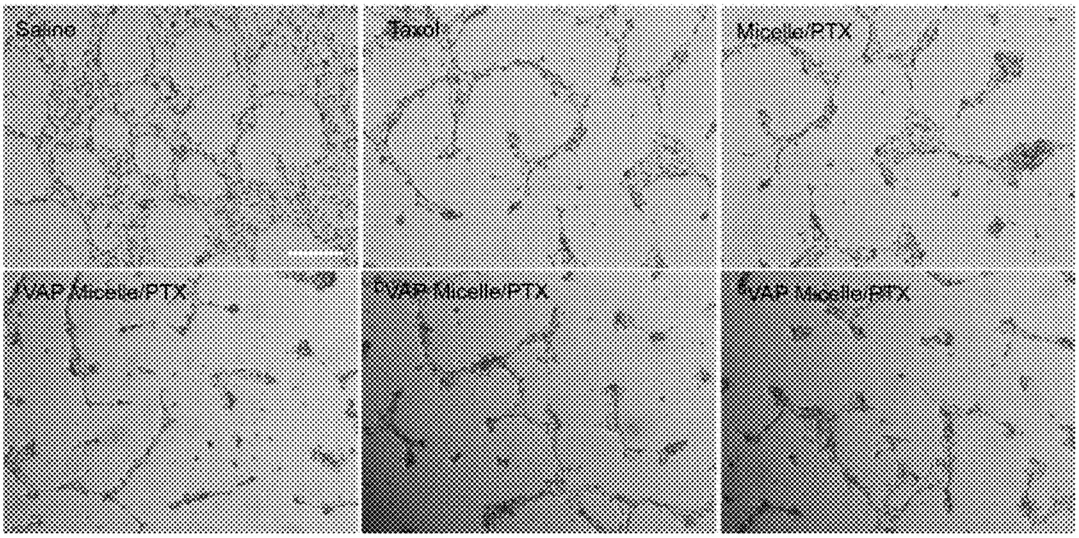
FIG. 29 shows the in vitro inhibition of the formation of neovascularization by paclitaxel loaded micelle: The figure shows the inhibition of mPEG-Micelle/PTX, $^{D}$VAP-Micelle/PTX, $^{S}$VAP-Micelle/PTX, $^{L}$VAP-Micelle/PTX and Taxol on in vitro neovascularization model, compared to $^{L}$VAP-Micelle/PTX, $^{D}$VAP-Micelle/PTX and $^{S}$VAP-Micelle/PTX inhibited the formation of neovascularization more significantly.

50 μL Matrigel basement was added into each well of 24-well culture plate and incubated for 30 min in a 37° C. incubator for coagulation. HUVEC cells were digested with 0.25% trypsin, and mixed with DMEM medium containing 1 μM paclitaxel VAP micelles or free paclitaxel drug solution to prepare single cell suspension, and cultured on the precoated 24-well culture plate at $1\times10^5$ cells per well at 37° C., 5% $CO_2$ and saturated humidity. The tube formation was observed after 12 hours (as shown in FIG. 29).

4. Inhibition Assay of Vasculogenic Mimicry by VAP-Micelle/PTX

50 μL Matrigel basement was added into each well of 24-well culture plate and incubated for 30 min in a 37° C. incubator for coagulation. U87 cells were digested with 0.25% trypsin, and mixed with DMEM medium containing 1 μM paclitaxel VAP micelles or free paclitaxel drug solution to prepare single cell suspension, and cultured on the precoated 24-well culture plate at $1\times10^5$ cells per well at 37°

Figure 30:
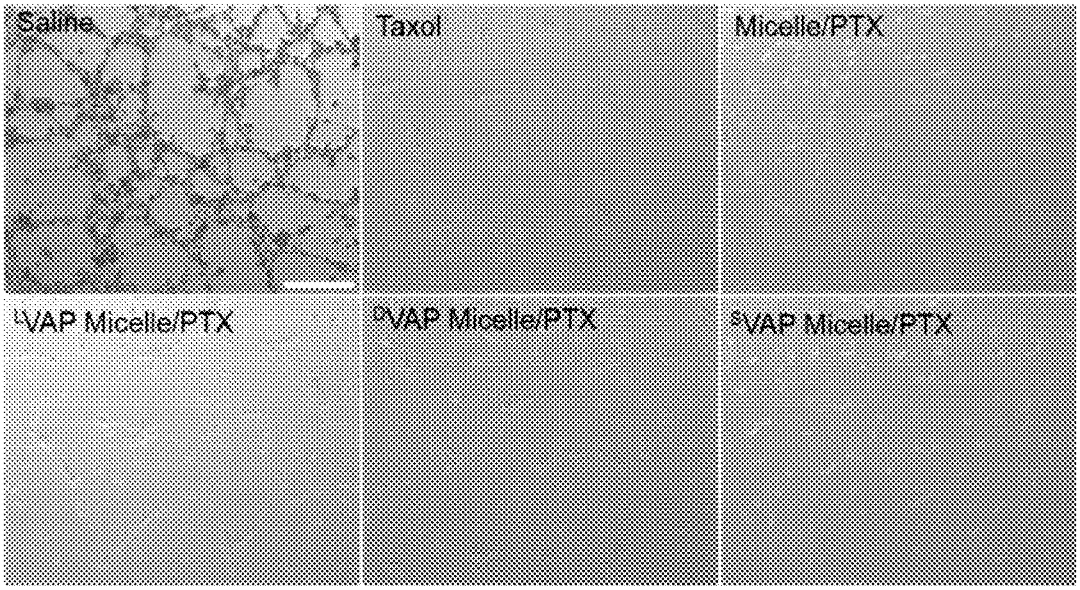
FIG. 30 shows the in vitro inhibition of the formation of vasculogenic mimicry by paclitaxel loaded micelles: The figure shows the inhibition of mPEG-Micelle/PTX, $^{D}$VAP-Micelle/PTX, $^{S}$VAP-Micelle/PTX, $^{L}$VAP-Micelle/PTX and Taxol on vasculogenic mimicry model compared to $^{L}$VAP-Micelle/PTX, $^{D}$VAP-Micelle/PTX and $^{S}$VAP-Micelle/PTX inhibited the formation of vasculogenic mimicry more significantly.

C., 5% $CO_2$ and saturated humidity. The tube formation was observed after 12 hours (as shown in FIG. 30).

EXAMPLE 11

In Vivo Anti-Glioma Efficacy Assay of VAP-Micelle/PTX

1. In vivo anti-glioma efficacy assay

The U87 subcutaneous tumor animal model was constructed and tested in groups when the tumor size was 100 $mm^3$. The subcutaneous tumor-bearing model mice were injected with 100 μl saline, Taxol, $^L$VAP-Micelle/PTX, $^D$VAP-Micelle/PTX, $^S$VAP-Micelle/PTX and mPEG-Micelle/PTX every three days for five times and the interval between each dose was 2 days. The total dose of paclitaxel was 25 mg/kg, The long diameter (a) and short diameter (b) of the tumor were measured by vernier calipers every other day and the tumor volume of nude mice was calculated according to the formula and the curve of tumor volume change with time was plotted, and the statistical difference of each group was calculated. The tumor volume of each group of nude mice was calculated according to the formula:

$$V_{tumor\ volume}=0.5(a \times b^2)$$

Figures 31A, 31B:
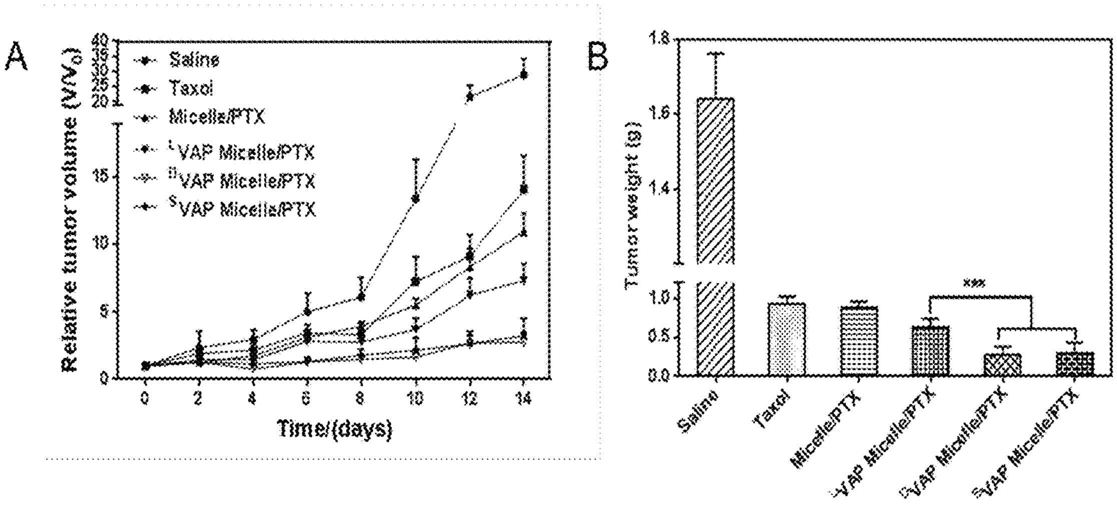
FIGS. 31A and 31B show the subcutaneous tumor growth inhibition of paclitaxel loaded micelles.

Eighteen days after the administration (24 days after the inoculation), all nude mice were sacrificed, the harvested subcutaneous tumors were weighed, and the statistical difference of each group were calculated (as shown in FIGS. 31A-31B).

2. Proapoptosis Assay of VAP-Micelle/PTX

Figure 32:
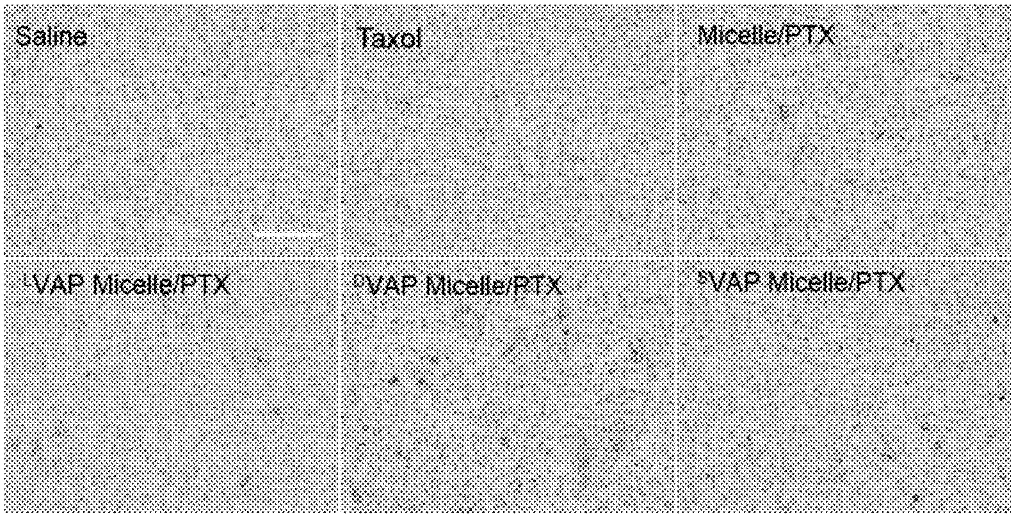
FIG. 32 shows the results of TUNEL staining: The figure shows the TUNEL staining pictures (bar=50 μm) of mPEG-Micelle/PTX, $^{D}$VAP-Micelle/PTX, $^{S}$VAP-Micelle/PTX, $^{L}$VAP-Micelle/PTX to promote tumor apoptosis, wherein the apoptotic cells showed brownish yellow or tan nuclei.

On the 14th day after administration completed, the tumors of the tumor-bearing nude mice were harvested and fixed for frozen sections, and tumor apoptosis was assayed by TUNEL. The procedure of terminal deoxynucleotidyl transferase-mediated dUTP nick end labeling (TUNEL) carried out to detect cell apoptosis was described as below: paraffin sections were conventionally dewaxed; rinsed with PBS for 3 times with 3 min each time; treated with 0.3% $H_2O_2$ solution at room temperature for 20 min; digested by 20 μg/mL proteinase K at 37° C. for 20 min; rinsed with PBS for 3 times with 3 min each time; each section was added with 30 μL of TUNEL solution (TDT and biotin-dNTP) and placed at 37° C. for 60 min. The positive result is that the nucleus is brownish yellow or tan, and the positive brown particles in the nucleus were considered as apoptotic cells. The number of apoptosis positive cells in 5 enlarged fields was counted continuously under an optical microscope, and the percentage of positive cells in the field was apoptosis index and the result is shown in FIG. 32.

3. Inhibition of Angiogenesis Assay of VAP-Micelle/PTX

Figure 33:
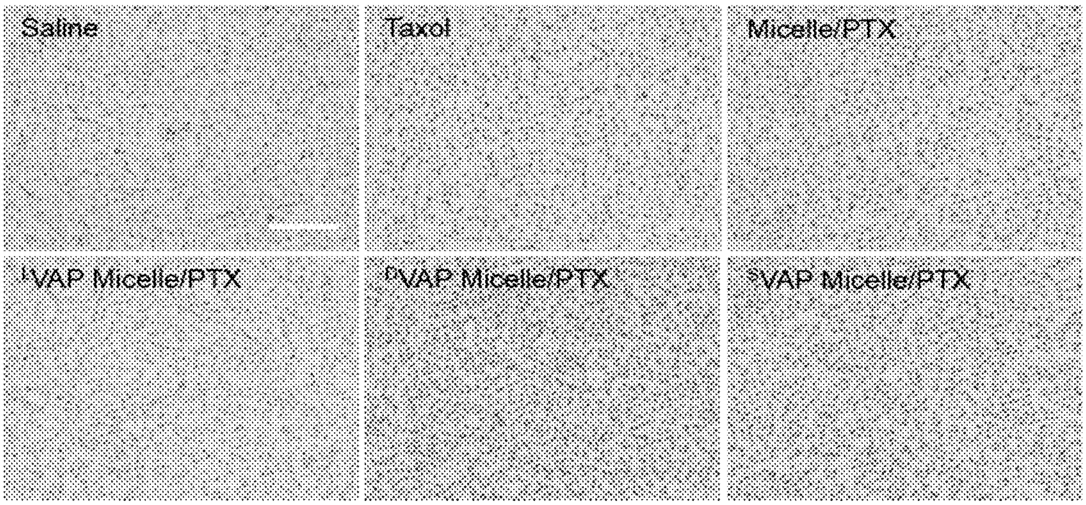
FIG. 33 shows the CD31/PAS double staining results: The figure shows the CD31/PAS staining pictures (bar=100 μm) of mPEG-Micelle/P TX, $^{D}$VAP-Micelle/PTX, $^{S}$VAP-Micelle/PTX, $^{L}$VAP-Micelle/PTX to inhibit neovascularization, wherein the nucleus of the neovascular cells is brownish yellow or tan.

On the 14th day after administration completed, the tumors of the tumor-bearing nude mice were harvested and fixed and embedded in paraffin and sectioned. CD31 immunohistochemical staining/periodic acid Schiff (PAS) dual staining was performed. The number of CD31 positive blood vessels in 5 enlarged fields was counted continuously under an optical microscope, and the result is shown in FIG. 33.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic (s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A peptide complex of $^{D}$VAP or $^{S}$VAP, wherein the $^{D}$VAP and/or $^{S}$VAP peptide complex is a maleimide-group-contained imaging substance modified by the $^{D}$VAP or $^{S}$VAP of, wherein the $^{D}$VAP or $^{S}$VAP is a D-configuration peptide having high affinity to GRP78 and the amino acid sequence of the $^{D}$VAP is $^{D}$P$^{D}$A$^{D}$V$^{D}$R$^{D}$T$^{D}$N$^{D}$S, and the amino acid sequence of the $^{S}$VAP is $^{D}$S$^{D}$N$^{D}$T$^{D}$R$^{D}$V$^{D}$A$^{D}$P; and wherein the structure of the $^{D}$VAP or $^{S}$VAP peptide complex is $^{D}$VAP-X and/or $^{S}$VAP-X, X is the image substance;

wherein the X is one or more selected from of the group consisting of a fluorescent substance, a near-infrared dye, a magnetic resonance imaging agent, and a radiographic agent.

2. The peptide complex of $^{D}$VAP and/or $^{S}$VAP according to claim 1, wherein the fluorescent substance is Fluorescein, the near-infrared dye is Cy7, IR820, and/or DiR, the magnetic resonance imaging agent is Gd-DTPA, and the radiographic agent is $^{99m}$Tc-DTPA.

3. A peptide complex of $^{D}$VAP or $^{S}$VAP, wherein the $^{D}$VAP or $^{S}$VAP peptide complex is an antitumor drug modified by the $^{D}$VAP or $^{S}$VAP peptide, wherein the structure of the $^{D}$VAP or $^{S}$VAP peptide complex is $^{D}$VAP-Y or $^{S}$VAP-Y, Y is the antitumor drug;

wherein the $^{D}$VAP or $^{S}$VAP is a D-configuration peptide having high affinity to GRP78 and the amino acid sequence of the $^{D}$VAP is $^{D}$P$^{D}$A$^{D}$V$^{D}$R$^{D}$T$^{D}$N$^{D}$S, and the amino acid sequence of the $^{S}$VAP is $^{D}$S$^{D}$N$^{D}$T$^{D}$R$^{D}$V-$^{D}$A$^{D}$P;

wherein the antitumor drug is one or more selected from of the group consisting of anthracyclines, doxorubicin, epirubicin, taxanes, taxol, docetaxel, cabazitaxel, camptothecins, amptothecin, hydroxycamptothecin, irinotecan, vinblastines, vincristine, vinorelbine, proteasome inhibitors, bortezomib, carfilzomib, lactones, parthenolide, peptide drugs, p53 activating peptide, melittin, scorpion venom peptide and antimicrobial peptides.

4. The peptide complex of $^{D}$VAP and/or $^{S}$VAP according to claim 3, wherein the antitumor drug is one or more selected from of the group consisting of doxorubicin containing ketone, epirubicin containing ketone; paclitaxel containing hydroxyl, docetaxel containing hydroxyl, camptothecin containing hydroxyl, hydroxycamptothecin containing hydroxyl, 9-nitro camptothecin containing hydroxyl, vincristine containing hydroxyl, etoposide containing hydroxyl, gemcitabine containing hydroxyl, cytarabine containing hydroxyl, 5-fluorouracil containing amino, teniposide containing hydroxyl, moritinib containing amino, epothilone containing hydroxyl, vinorelbine containing hydroxyl, actinomycin D containing amino, mitoxantrone Anthraquinone containing hydroxyl, mitomycin containing amino, bleomycin containing hydroxyl and amino, irinotecan containing hydroxyl,; bortezomib containing boric acid, carfilzomib containing amino; peptide drugs of p53 activating peptide, melittin and scorpion venom peptide.

5. A peptide complex of $^{D}$VAP or $^{S}$VAP, wherein, the $^{D}$VAP or $^{S}$VAP peptide complex is a polymer carrier material modified by the $^{D}$VAP and $^{S}$VAP, wherein the $^{D}$VAP or $^{S}$VAP is a D-configuration peptide having high affinity to GRP78 and the amino acid sequence of the $^{D}$VAP is $^{D}$P$^{D}$A$^{D}$-V$^{D}$R$^{D}$T$^{D}$N$^{D}$S, and the amino acid sequence of the $^{S}$VAP is $^{D}$S$^{D}$N$^{D}$T$^{D}$R$^{D}$V$^{D}$A$^{D}$P; and wherein the structure of the $^{D}$VAP and $^{S}$VAP peptide complex is $^{D}$VAP-polyethylene glycol-Z and $^{S}$VAP-polyethylene glycol-Z, Z is the polymer carrier material;

wherein the polymer carrier material is one or more selected from of the group consisting of phospholipids, polylactic acid, poly lactic-co-glycolic acid, and polycaprolactones.

6. A drug delivery system, characterized in that, the drug delivery system comprises:

D-configuration peptide having high affinity to GRP78, wherein the D-configuration peptide is $^{D}$VAP or $^{S}$VAP, and the amino acid sequence of the $^{D}$VAP is $^{D}$P$^{D}$A$^{D}$-V$^{D}$R$^{D}$T$^{D}$N$^{D}$S, and the amino acid sequence of the $^{S}$VAP is $^{D}$S$^{D}$N$^{D}$T$^{D}$R$^{D}$V$^{D}$A$^{D}$P; and/or $^{D}$VAP and/or $^{S}$VAP peptide complex, wherein the drug delivery system is a liposome delivery system, a polymer micelle delivery system, a polymer disc delivery system or a nanoparticle delivery system.

7. The drug delivery system according to claim 6, characterized in that, besides the $^{D}$VAP and/or $^{S}$VAP peptide complex, the drug delivery system further comprises: (1) a diagnostic drug, (2) an antitumor drug, or both;

wherein the (1) diagnostic drug is one or more selected from of the group consisting of fluorescent substance, near-infrared dye and magnetic resonance imaging agent, and/or the (2) anti-tumor drug is one or more selected from of the group consisting of anthracyclines, doxorubicin, epirubicin, taxanes, taxol, docetaxel, cabazitaxel, camptothecins, camptothecin, hydroxycamptothecin, irinotecan, vinblastines, vincristine, vinorelbine, proteasome inhibitors, bortezomib, carfilzomib, Intones, parthenolide, peptide drugs, p53 activating peptide, melittin, peptide drugs, scorpion venom peptide and antimicrobial peptides.

8. The drug delivery system according to claim 6, wherein the $^{D}$VAP and/or $^{S}$VAP peptide complex is the peptide complex of $^{D}$VAP and/or $^{S}$VAP of claim 5, and the drug delivery system is a liposome delivery system, a polymer micelle delivery system, a polymer disc delivery system, or a nanoparticle delivery system.

9. The drug delivery system according to claim 6, wherein drug delivery system is used for the diagnosing, tracing, and/or treating a tumor.

10. The drug delivery system according to claim 7, wherein the fluorescent substance is Fluorescein, the near-infrared dye is selected from Cy7, IR820, DiR, and/or the magnetic resonance imaging agent is Gd-DTPA.

11. A method for tumor diagnosis and/or targeted therapy comprising administering to a subject in need thereof:

the peptide complex of $^{D}$VAP or $^{S}$VAP according to claim 1.

12. The method according to claim 11, wherein the tumor is glucose-regulating protein GRP78 high expressed tumor.

13. A method for tumor diagnosis and/or targeted therapy, comprising administering to a subject in need thereof:

peptide complex of $^{D}$VAP or $^{S}$VAP according to claim 3.

14. The method according to claim 13, wherein the tumor is glucose-regulating, protein GRP78 high expressed tumor.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: Synthetic: DVAP

<400> SEQUENCE: 1

Pro Ala Val Arg Thr Asn Ser
1               5


<210> SEQ ID NO 2
<211> LENGTH: 7
<212> TYPE: PRT
<213> ORGANISM: Artificial Sequence
<220> FEATURE:
<223> OTHER INFORMATION: Synthetic: SVAP

<400> SEQUENCE: 2

Ser Asn Thr Arg Val Ala Pro
1               5


<210> SEQ ID NO 3
<211> LENGTH: 7
<212> TYPE: PRT
<213> ORGANISM: Artificial Sequence
<220> FEATURE:
<223> OTHER INFORMATION: Synthetic: LVAP

<400> SEQUENCE: 3

Ser Asn Thr Arg Val Ala Pro
1               5


<210> SEQ ID NO 4
<211> LENGTH: 8
<212> TYPE: PRT
<213> ORGANISM: Artificial Sequence
<220> FEATURE:
<223> OTHER INFORMATION: Synthetic: DVAP-Cys

<400> SEQUENCE: 4

Cys Pro Ala Val Arg Thr Asn Ser
1               5


<210> SEQ ID NO 5
<211> LENGTH: 8
<212> TYPE: PRT
```

-continued

<213> ORGANISM: Artificial Sequence
<220> FEATURE:
<223> OTHER INFORMATION: Synthetic: LVAP-Cys / SVAP-Cys

<400> SEQUENCE: 5

Ser Asn Thr Arg Val Ala Pro Cys
1 5